(12) United States Patent
Paz

(10) Patent No.: US 8,360,972 B2
(45) Date of Patent: Jan. 29, 2013

(54) VIRTUAL PORTS DEVICES AND METHOD

(76) Inventor: Adrian Paz, Petah Tikwa (IL)

(*) Notice: Subject to any disclaimer, the term of this patent is extended or adjusted under 35 U.S.C. 154(b) by 0 days.

(21) Appl. No.: 13/160,528

(22) Filed: Jun. 15, 2011

(65) Prior Publication Data

US 2011/0245596 A1    Oct. 6, 2011

Related U.S. Application Data

(63) Continuation of application No. 10/563,229, filed as application No. PCT/IL2004/000593 on Jul. 2, 2004, now Pat. No. 8,038,612.

(30) Foreign Application Priority Data

Jul. 2, 2003 (GB) .................................. 0315479.6
Oct. 24, 2003 (GB) .................................. 0324830.9

(51) Int. Cl.
*A61B 1/32* (2006.01)

(52) U.S. Cl. ........................................ 600/235; 600/210
(58) Field of Classification Search ................. 600/201, 600/204, 207, 37, 235; 128/899
See application file for complete search history.

(56) References Cited

FOREIGN PATENT DOCUMENTS

WO    WO 03/097124    * 11/2003

* cited by examiner

*Primary Examiner* — Andrew Yang
(74) *Attorney, Agent, or Firm* — Daniel J. Swirsky; AlphaPatent Associates Ltd.

(57) ABSTRACT

A device auxiliary to surgery, for anchoring and lifting cavity walls or internal organs of a patient. The device provides a virtual port; that is an instrument that can be non-invasively, or minimally invasively and removably attached to the undersurface of a patient's cavity, or to various tissues within a cavity, and to which various retracting means are attached. The device includes means allowing it to be moved from one position to another and reattached to the undersurface of the abdominal wall, or to various tissues within a cavity, without creating any additional openings in the cavity wall. The device includes means for attaching various retractors.

8 Claims, 27 Drawing Sheets

VIRTUAL PORTS DEVICES AND METHOD

CROSS-REFERENCE TO RELATED APPLICATIONS

This application is a continuation under 35 U.S.C. 120 of U.S. patent application Ser. No. 10/563,229, Jan. 3, 2006 now U.S. Pat. No. 8,038,612 which is a U.S. National Phase Application under 35 U.S.C. 371 of PCT International Application No. PCT/IL2004/000593, which has an international filing date of Jul. 2, 2004, and which claims priority benefit from UK Patent Application No. 0315479.6, filed Jul. 2, 2003, and UK Patent Application No. 0324830.9, filed Oct. 24, 2003, incorporated herein by reference in their entirety.

FIELD OF THE INVENTION

This invention concerns devices auxiliary to surgery.

The invention relates in particular to such devices for anchoring and lifting cavity walls or internal organs of a patient and for holding surgical instruments.

BACKGROUND OF THE INVENTION

This invention relates to anchoring devices for retractors and/or for lifting the cavity walls, being attached to the internal surface of a cavity or to various organs within a cavity, during minimally invasive surgery.

More specifically, the invention relates to minimally invasive or preferentially non-invasive anchoring system and devices for attachment to the internal walls of the cavity, or on the organs within a cavity in which the intervention is performed, at another location than the orifice through which they were originally introduced.

Preferably, the device can be moved and re-attached, one or more times, non-invasively or minimally invasively, to other locations in the interior of the cavity. Such devices are denoted throughout the patent application as virtual ports. The purpose of such virtual port devices is to supply an anchoring device for retracting various tissue and organs by self-retained retractor means, or to supply an anchoring device for instruments which are attached to these virtual port devices.

This anchoring permits instruments within the cavity to be moved in any possible direction and at any angle. Such devices may comprise attachment of the device on the underside of the cavity, or on internal organs and tissues, by magnetic attachment means, suction attachment, adhesive attachment, mechanical attachment by small barbs, or clips, other minimally invasive means such as wires introduced through the entire thickness of the cavity wall and attached to the anchoring device on the internal side of the cavity, any combination of these modalities, or other non-invasive or minimally invasive anchoring means that might be envisioned for those accustomed to the art.

Additionally, in case the anchoring device is held in place by a device situated on the on exterior surface of a cavity such as the abdomen, these devices may serve also for lifting the cavity wall and permit performance of atmospheric pressure laparoscopy. The devices on the outer surface of the cavity can be attached to a frame or to rods fixed to the operating table, to the operating room floor or ceiling and serve for lifting the cavity wall, permitting to perform the intervention without the necessity to insufflate the cavity with gas.

Gas insufflation has its potential drawbacks such as generation of positive pressure, which in case of abdominal laparoscopy can be detrimental in obese patients, patients with chronic respiratory and/or cardiac diseases.

Additionally gas insufflation, necessitates an insufflator device, can result in rapid loss of the working cavity when there is a gas leak, or when the gas exhaust results in inadequate view of the surgical site.

Laparoscopic interventions represent a significant advance in various fields of surgery permitting the performance of the majority of interventions through a number of small incisions reducing postoperative pain and enhancing the postoperative recovery. However there are still a significant number of drawbacks to this technique. The fixed position of the access openings in the wall of the cavity—access ports—significantly limits the approach to some surgical locations making some interventions very long and technically demanding. Creation of additional ports may negate the minimal invasive nature of the procedure. Some ports are used mainly for introducing retracting instruments in order to facilitate dissection.

The fixed position of the ports may hinder retraction in various directions, and the limited potential access sites (as for example anterior and lateral walls, but not posterior, proximal and distal walls of the abdomen for abdominal laparoscopy) may make retraction in some directions impossible.

Magnetic attraction has been used in medicine to remotely attach devices to tissue, or to remotely manipulate tissue. So, in U.S. Pat. No. 6,358,196, issued to RAYMAN REIZA magnetic substances are introduced into the intestine by ingestion and the intestines are remotely manipulated by an electromagnet during laparoscopic surgery. However this device does not permit retraction of an abdominal organ other than intestine and does not permit precise retraction of a particular segment of intestine.

In patents US2003009080, U.S. Pat. No. 6,494,211, a suction device is used to attach a retractor to various organs such as the heart in order to retract it in a specific direction. However these devices are introduced trough orifices in the body wall and they are not virtual ports since they can not permit non invasive anchoring of the retractor to the undersurface of the cavity wall, or within the cavity in another location than the access port.

In patents WO03013366, U.S. Pat. No. 6,206,827 a retractor device is attached to the organ to be retracted by some adhesive. However, the retractors are introduced through an orifice and do not represent a virtual port since they can not permit non invasive anchoring of the retractor to the undersurface of the cavity wall, or within the cavity in another location than the access port.

In U.S. Pat. No. 6,206,827, a retractor is directly attached to tissue by penetrating it with mechanical sharp means such as barbs or springs and traction on this means cause tissue retraction. However, the retractors are introduced through an orifice and do not represent a virtual port since they can not permit non invasive anchoring of the retractor to the undersurface of the cavity wall, or within the cavity in another location than the access port.

In patents EP1287786, U.S. Pat. No. 5,690,607 abdominal wall retractors that may be used for gasless laparoscopy are described. However, these devices can be used only for lifting the body wall and cannot be used, neither for anchoring endoscopic graspers, necessary for retracting intra-abdominal tissues and organs, nor for anchoring instruments at various position on the undersurface of the abdominal cavity. Additionally, when using rods for retraction, a few mm orifices are performed in the body wall.

There is a need for an anchoring device that is non invasively and removably attached to the undersurface of a cavity, or to various tissues within a cavity, or to tissues within a cavity, during minimally invasive surgery acting as an anchoring device for a retractor.

There is a need for an anchoring device, to which various retractors are attached, that is non invasively and removably attached to the interior surface of a cavity, or to various tissues within a cavity, and that can be moved to any other position easily.

There is a need for such an anchoring device that is noninvasively and removably attached to the interior surface of a cavity by magnetic attraction using a magnet or electromagnet on the exterior surface of the cavity.

There is a need for an anchoring device that is non-invasively and removably attached to the interior surface of a cavity, or to various tissues within a cavity, by using suction.

There is a need for an anchoring device that is non-invasively and removably attached to the interior surface of a cavity, or to various tissues within a cavity, by using suction in which the suction is applied continuously or in which the suction tube is detachable.

There is a need for an anchoring device that is non-invasive and removably attached to the interior surface of a cavity, or to various tissues within a cavity, by using a pressure sensitive gel or other reversible adhesive means.

There is a need for an anchoring device that is minimally invasive and removably attached to the interior surface of a cavity, or to various tissues within a cavity, using mechanical means such as barbs, or fixation wires.

There is a need for an anchoring device that is non-invasively or minimally invasively and removably attached to the interior surface of a cavity, that can permit lifting the cavity wall for performing gasless laparoscopy There is a need for an anchoring device that is non-invasively and removably attached to the interior surface of a cavity, or to various tissues within a cavity, using any combination of the above means.

Applicant believes these needs are not answered in prior art, as well as other problems which will become apparent upon reading the present disclosure.

SUMMARY OF THE INVENTION

It is an object of the present invention to provide a new surgery device including means for anchoring and lifting cavity walls or internal organs of a patient.

The device provides a virtual port, that is, an instrument that can be non-invasively, or minimally invasively and removably attached to the undersurface of a patient's cavity, or to various tissues within a cavity, and to which various retracting means or instruments are attached.

The device includes means allowing it to be moved from one position to another and reattached to the undersurface of the abdominal wall, or to various tissues within a cavity, without creating any additional openings in the cavity wall.

The device includes means for attaching various retractors, etc.

In a preferred embodiment, the device uses a pair of solid magnets, with an inner and an outer part.

The retractor means may comprise a self retaining clamp or other mechanical attachment means, a vacuum activated attachment means, a adhesive attachment means such as a pressure adhesive gel or a combination thereof.

In another embodiment, the virtual port device comprises an inflatable chamber, which can be filled with a magnetisable gel or emulsion, or by magnetisable particles.

In yet another preferred embodiment, the virtual port device is provided with a suction device that allows attaching the device to the interior surface of the cavity or to various tissues within a cavity.

In another preferred embodiment, the virtual port device comprises a suction cup with an elastic membrane, which is coated on its tissue facing surface with a pressure sensitive adhesive gel that permit better attachment to the cavity wall, or to various tissues within a cavity.

In another preferred embodiment, the virtual port anchoring device is attached to the inner side of the cavity by small barbs that penetrate the tissue when the device is pressed by the introducer against it.

In another preferred embodiment, the virtual port anchoring device is attached to the inner side of the cavity by wires that penetrate and pierce the cavity wall. Preferably, the attachment device is shaped as an umbrella that opens on the undersurface of the cavity and is held in this position by and prevented from flipping back on itself by some reinforcing means.

In another preferred embodiment, the virtual port anchoring device is attached to the inner side of the cavity by a self-retaining clamp.

The embodiments in which the anchoring means are held in place by some device on the outer surface of the cavity, such as by magnetic attraction or by wires piercing the entire thickness of the cavity, can serve also for gasless (atmospheric pressure) endoscopy or laparoscopy.

The anchoring device may serve also for anchoring and as a hinge for instruments, etc.

The surgeon may use one hole in the abdomen for inserting surgical instruments, and a plurality of anchoring sites having a minimal diameter, for holding and manipulating these instruments.

Further objects, advantages and other features of the present invention will become obvious to those skilled in the art upon reading the disclosure set forth hereinafter.

BRIEF DESCRIPTION OF THE DRAWINGS

The invention will now be described by way of example and with reference to the accompanying drawings in which.

DETAILED DESCRIPTION THE INVENTION

A preferred embodiment of the present invention will now be described by way of example and with reference to the accompanying drawings.

The device of the present invention provides a virtual port, that is, an instrument that can be non-invasively and removably attached to the undersurface of a patient's cavity, or to various tissues within a cavity, and to which various retracting means are attached.

The device is initially introduced through an opening in the cavity wall and then attached to some location on the undersurface of the cavity wall, or to various tissues within a cavity, by some non-invasive attachment means.

Figure 1:
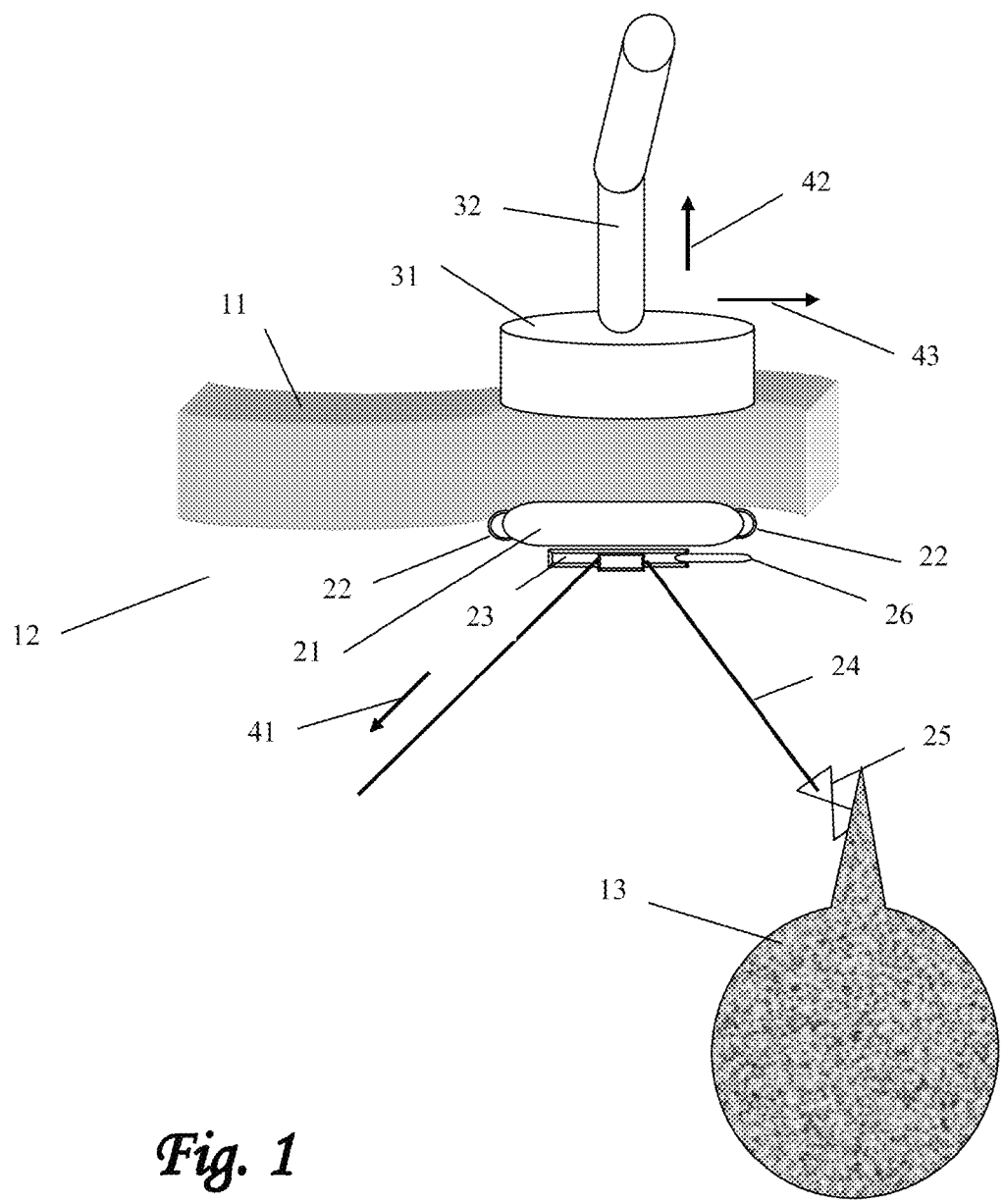
FIG. 1 virtual anchoring point device with internal magnet

FIG. 1 illustrates a virtual anchoring point device with internal magnet, to attach to an abdominal wall 11 of the abdominal cavity 12, inside the human body. There is an outer magnet or electromagnet 31, connected to holding/moving means 32, such as an articulate arm or robot arm or manual holding handle. The outer magnet can be secured to the ceiling or a wall or another fixed spot. The system also includes an inner magnet 21, or body having ferromagnetic properties. A terminal loop or protuberance 22, at one or both ends of the elongated body of magnet 21, is used to pull it in or out of the human body.

The device also includes a ratchet mechanism 23, which holds the string 24 after it is pulled in the direction shown with arrow 41, then the clips 25 attached to the other side of wire 24, pulls the internal organ 13 to which it is attached.

A lever 26 when activated, releases the ratchet mechanism 23, so that the tension in wire 24 is released, to stop pulling the internal organ 13

Dual use of device:

1. to hold open the internal body cavity 12, such as the abdominal cavity by applying a force outwards, generally in the direction of arrow 42. The body cavity can thus be kept open, filled with gas at about atmospheric pressure—no higher pressure is required.

2. to act as virtual anchor point to pull internal organs 13 towards it. one or more organs can be pulled towards the anchor point The inner magnet 21 can be moved to another location by moving the outer magnet 31 laterally, as indicated with the arrow 43. The device can be moved from one position to another and reattached to the undersurface of the abdominal wall, or to various tissues within a cavity, without creating any additional openings in the cavity wall.

In a preferred embodiment, the device includes a solid magnet that can be introduced through an opening in a cavity wall such as the abdominal wall.

The device shape is spherical or elongated and enough magnetisable substance is incorporated to permit effective attraction by a magnet on the exterior surface of the cavity. The device is smoothed, or coated with a smooth coating permitting it to slide easily on the undersurface of the cavity.

To the virtual port device may be attached, through a string, a tissue attachment means. This system will cause retraction by pulling toward the anchoring means. Alternatively, instead of a string, a rod may be attached to the anchoring means, serving to push away the tissue from the anchoring device.

The device is preferably polished, processed to achieve a smooth outer surface, or coated with a smooth coating permitting it to slide easily on the undersurface of the cavity, or on various tissues within a cavity.

To the virtual port device is attached, through a string, a tissue grasping means. The attachment means may represent a self retaining clamp, grasper, or other mechanical attachment means, a vacuum activated attachment means, an adhesive attachment means such as a pressure adhesive gel or a combination thereof. This system will cause retraction by pulling toward the anchoring means.

Alternatively, instead of a string, a rod may be attached to the anchoring means serving to push away the tissue from the anchoring device. Also, a combination of pulling and pushing retractor means may be used.

The grasping means of the tissue retractor may include a self-retaining clamp or other mechanical attachment means, a vacuum activated attachment means, a adhesive attachment means such as a pressure adhesive gel or a combination thereof.

Additionally, the grasping means may be directly to the tissue to be retracted, or to a net, to an elastic sheet, a balloon device, or any combination thereof of such devices, which serve for tissue or organ retraction.

The string that connects the attachment means to the device may be an elastic string, or an adjustable length string, whose length can be adjusted by pulling it through a self locking ratchet mechanism, with a means for manual or remote release of the string tension, or using other mechanisms such as springs, that may be envisioned by those accustomed to the art.

Also, strings of various lengths and various tensile strengths and elasticity may be removably attached to the virtual port device using an interlocking or other simple attachment means.

The magnet on the undersurface of the cavity is maintained attached to the abdominal wall by using a magnet or electromagnet on the exterior surface of the cavity. Using a strong enough magnetic field, enough attraction force can be applied to the undersurface magnet, which is at a distance of a few cm or more from the upper surface magnet, and permitting it to hold weight of a few hundred grams, as necessary for tissue and organ retraction. The undersurface magnet, included in the virtual port device, may be advanced to a new position by moving the magnet on the exterior surface of the cavity.

When large electromagnets are needed these may be held above the patient by an articulated arm that may be manipulated manually or by specific engines to the desired position.

Figure 2:
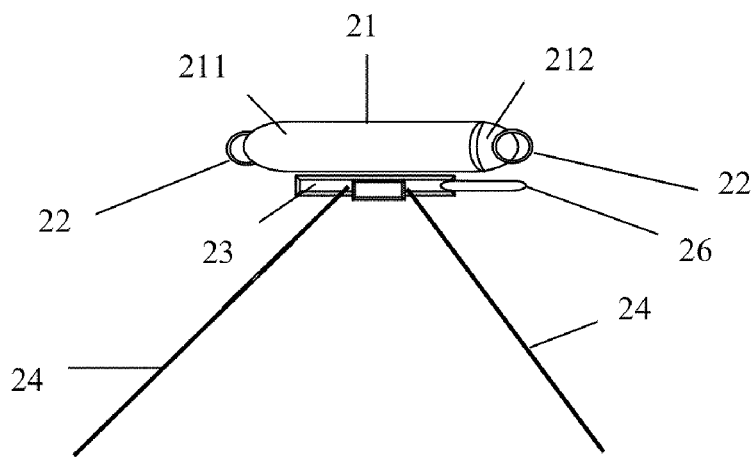
FIG. 2 details the internal magnet

FIG. 2 details the internal magnet 21, having an elongated shape, preferably cylindrical with rounded ends 211,212 for easy insertion into the body and extraction therefrom.

In another embodiment, the virtual port device comprises an inflatable chamber, which can be filled with a magnetisable gel or emulsion, or by magnetisable particles. This device can be introduced in a deflated situation through a slender port and inflated by a liquid or semi-liquid substance to a larger volume permitting better attraction by the magnetic field. The inflatable chamber can be connected to an inflating tube continuously or it can be detachably connected to such a tube in which case, one or more one-way valve are provided to prevent spillage.

Such valve means may be provided with a flexible and broad connection means that permit reattachment of the tube at various angles.

The device may be spherical, in which case a single connection means situated on the side opposite to the attachment side to the cavity wall.

The device may be spherical in which case a single connection means situated on the side opposite to the attachment side to the cavity wall.

Alternatively, the device may be elongated, in which case more than one connections means and one-way valves may be necessary to be able to reattach the tube to the device from various angles and positions.

Figure 9:
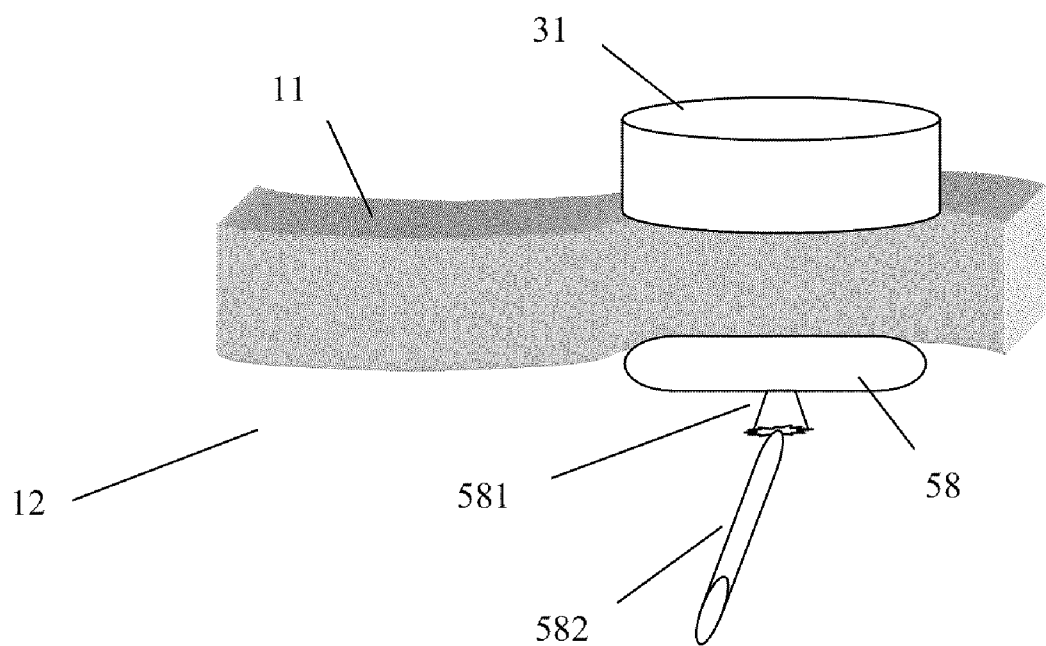

FIG. 9 details an inner body 58 which can be filled with a fluid magnetic filling through a tube 582 and valve 581. It is then attracted to an outer magnet or electromagnet 31.

The fluid ferromagnetic material may include, for example: small iron spheres in a gel mixture, or iron powder in oil.

In another preferred embodiment the virtual port device is provided with a suction device that permits attachment of the device to the interior surface of the cavity or to various tissues within a cavity. In this case the exterior wall of the device is shaped preferentially as a cup that is preferentially of reduced elasticity, that permit the device to be introduced through a small orifice but does not allow it to completely collapse when applying vacuum for suction attachment to the tissue. In some embodiments the cup is reinforced with radial ribs to prevent its collapse.

However, the device may be rigid, or elastic. The interior surface is provided with an elastic and impermeable membrane that is sucked in when applying vacuum to the inside of the suction device. The suction cup is provided at its periphery with a sealing rim, shaped as a flange and manufactured from a foamy plastic material or similar material that permits effective sealing and prevent loss of vacuum. Between the membrane and the interior surface of the cup a chamber is created.

Additionally, the elastic membrane may be provided with one or more orifices that permit better suction and attachment.

Alternatively, the suction cup may be applied directly to the tissue without an intervening membrane.

In some embodiments an absorbent material is provided inside the suction cup to prevent pooling of liquid, between the suction device and tissue and detachment of the suction device.

The grasping means may be directly to the tissue to be retracted, or to a net, or to an elastic sheet, rod, balloon device, or to any combination thereof, which serve for tissue or organ retraction. The string that connect the attachment means to the device may be an elastic string, or an adjustable length string, whose length can be adjusted by pulling it through a self locking ratchet mechanism, with a means for manual or remote release of the string tension, or using other mechanisms such as springs, that may be envisioned by those accustomed to the art. Also, strings of various lengths and various tensile strengths and elasticity may be removably attached to the virtual port device using an interlocking or other simple attachment means.

Alternatively, the device may be elongated, in which case more than one connections means and one-way valves may be necessary to be able to reattach the tube to the device from various angles and positions. The connector used for attaching the canula may be of a mechanical articulation type for example a bayonet connection, or by using an inflatable balloon at the end of the canula to firmly attach it to a proper cavity on the anchoring device.

Figure 3:
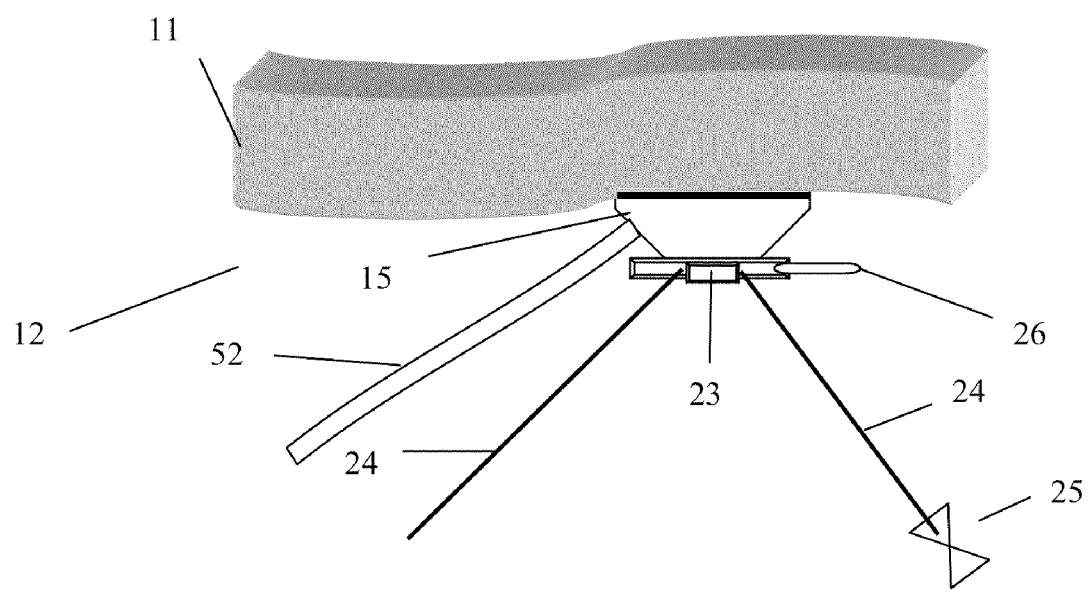
FIG. 3 details a virtual port using a vacuum cup with vacuum tube

FIG. 3 details a virtual port using a vacuum cup with vacuum tube, to attach to the abdominal wall 11. In the abdominal cavity 12—inside the human body—is inserted a vacuum cup 51, which is flexible/collapsible and connected to vacuum tube 52. The string 24, after being pulled in the direction shown, will pull an internal organ.

A ratchet mechanism 23 holds the tension in the string. A clips 25 attached to the other side of string 24, connects to an internal organ as desired.

Figure 4:
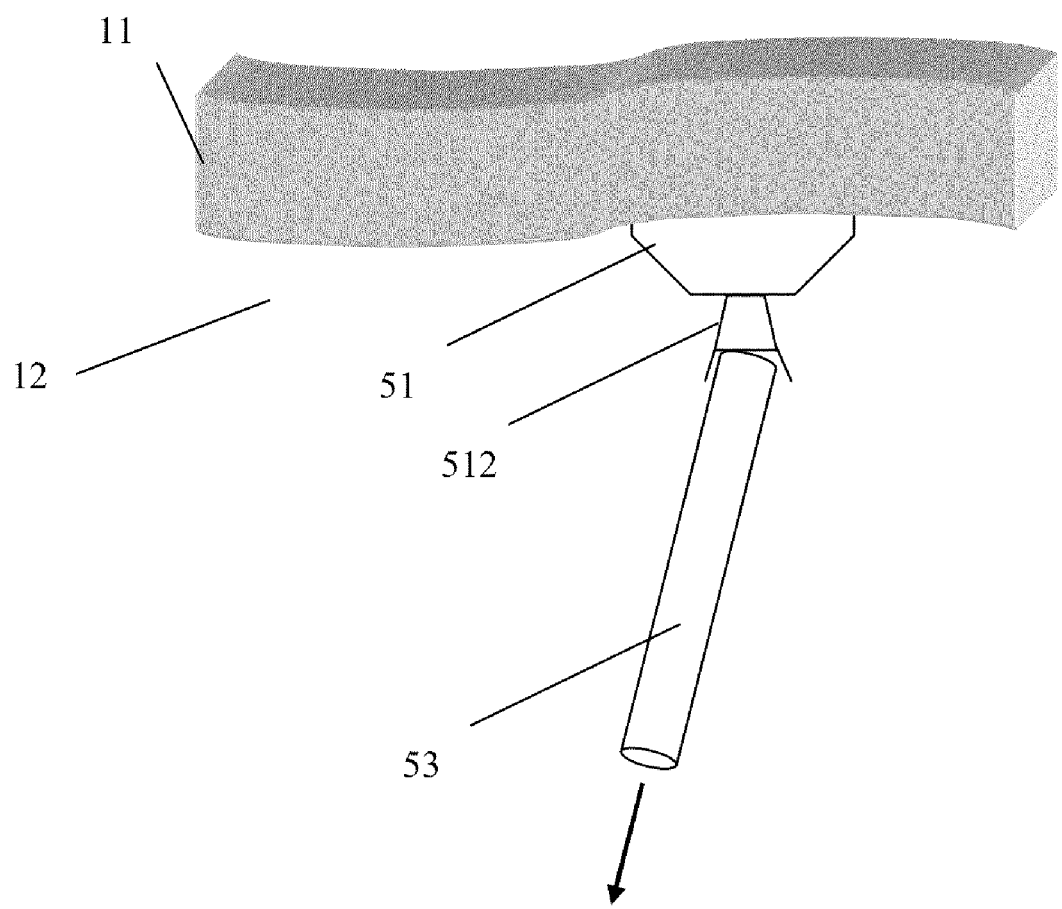
FIG. 4 details a virtual port using a vacuum cup with detachable canula

FIG. 4 details a virtual port using a vacuum cup with detachable canula, to attach to the abdominal wall 11. The device has a vacuum cup 51, coupled with a vacuum canula 53 through a cup receptacle 512, which receives the canula 53.

In a preferred embodiment the vacuum device is provided with a vacuum accumulator or reservoir, represented by a non collapsible chamber connected to the cup by a one directional valve, that may prevent vacuum lose during the time that the cup is applied to the undersurface of the cavity. The exterior wall of the suction device is connected through a slender tube to a vacuum source, this connection may be fixed or detachable; in the latter case, one or more one-way valves are provided to prevent vacuum loss when in detached state. Such valve means may be provided with a flexible and broad connection means that permit reattachment of the tube at various angles. The connector used for attaching the canula may be of a mechanical articulation type for example a bayonet connection, or by using an inflatable balloon at the end of the canula to firmly attach it to a proper cavity on the anchoring device.

Figure 5:
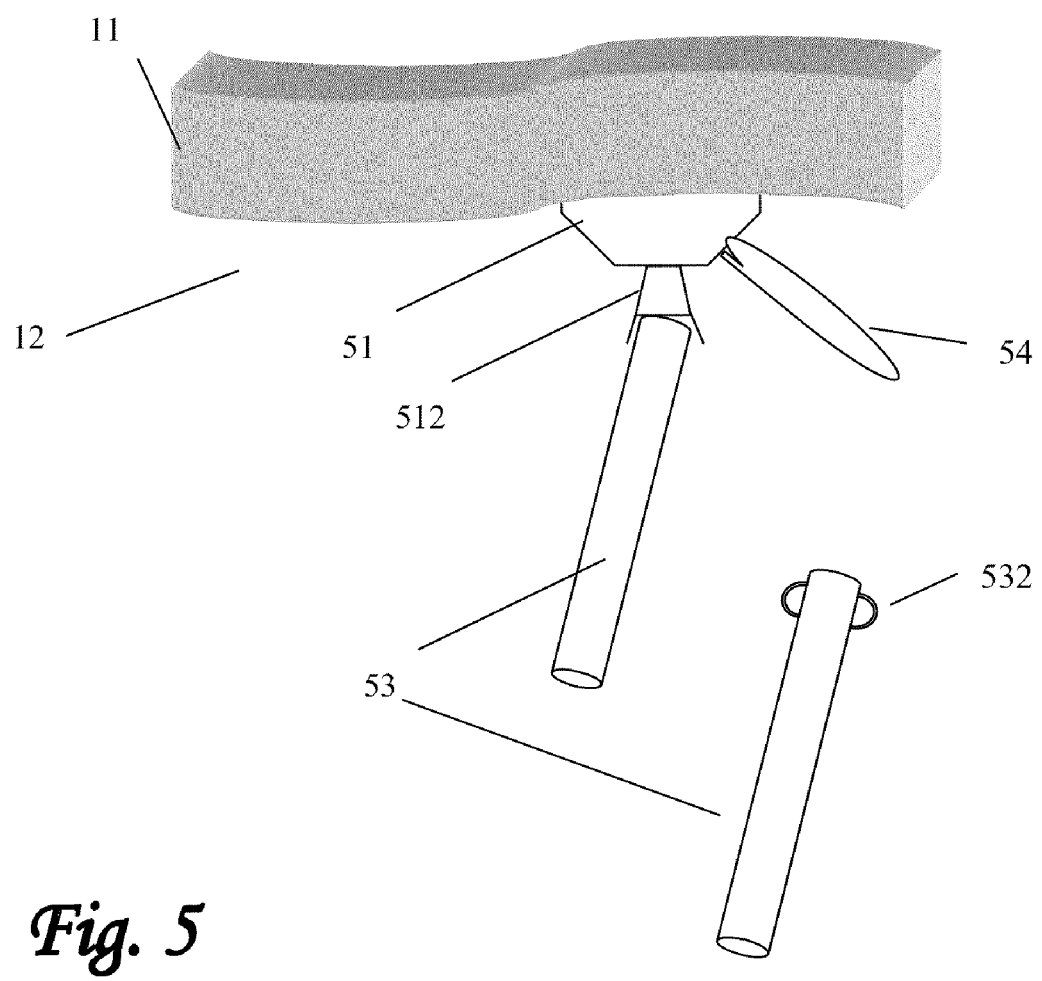
FIG. 5 details a virtual port using a vacuum cup with canula and vacuum reservoir FIG. 6 details a vacuum/magnetic cup with canula FIG. 7 details a virtual port including a wire with a reversed umbrella-shaped device before being attached into place FIG. 8 details a virtual port use of a wire with a reversed umbrella-shaped device attached into place FIG. 9 details an inner body with fluid magnetic filling FIG. 10 details a virtual port self retaining clips FIG. 11 details the structure of a virtual port self retaining clips FIG. 12 details another embodiment of a virtual port self retaining clips FIG. 13 details a virtual port self retaining clips with a vacuum cup/grasping means FIG. 14 details a net for holding internal organs or pushing them aside FIG. 15 details means for holding an internal organ by attaching it to a virtual port FIG. 16 details a balloon with affixed virtual port devices FIG. 17 details vacuum cup with a two-state valve in its Closed state FIG. 18 details vacuum cup with a two-state valve in its Open state

FIG. 5 details a virtual port using a vacuum cup with canula and vacuum reservoir, including a vacuum cup 51, a vacuum canula 53 with vacuum reservoir 54 with valve to cup 51. If gas enters the cup 51 to lower the vacuum level in cup 51, the reservoir 54 will help maintain the vacuum in the cup 51.

A cup receptacle 512, receives the canula 53 with optionally inflating balloon 532 to hold it there during the vacuum process alternately, the canula can connect to the reservoir 54, to create a higher level of vacuum there—about 0.1 atmosphere, only part of it being created in the vacuum cup 51 (about 0.3-0.5 atmospheres) so as not to damage tissue.

In another embodiment, the virtual port device is removably attached to the interior surface of the working cavity, or to tissue within the working cavity, by adhesive means such as but not limited to a pressure sensitive gel.

Attachment to the interior surface of the cavity, or to tissue within the working cavity, may be obtained by any combination of the above mentioned means. In a preferred embodiment, the virtual port device comprises a magnet means and suction means. This combination permits using a less bulky magnet mainly for moving the virtual port from one position to another.

During changing the position, the vacuum is reduced and the electromagnet is moved on the upper surface of the cavity to the new location dragging the virtual port device to its new position on the interior surface of the cavity.

Figure 6:
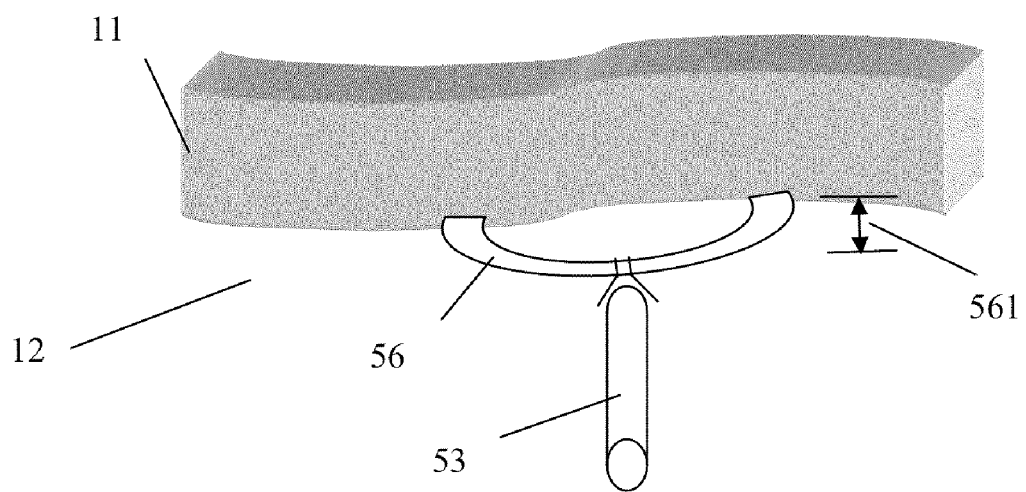

FIG. 6 details use of a vacuum/magnetic cup with canula, including a vacuum/magnetic elongated cup 56. The cup height 561 is about 1 cm.

A vacuum canula 53 is used to attach to the abdominal cavity 12—inside the human body.

In another preferred embodiment, the virtual port device comprises a suction cup with an elastic membrane, which is coated on its tissue facing surface with a pressure sensitive adhesive gel that permit better attachment to the cavity wall, or to various tissues within a cavity. The pressure sensitive adhesion gel and elastic membrane may be permeable to gas and/or liquids and an absorbent substance inside the suction cup may be provided too.

The spherical or elongated device is introduced into a cavity such as the abdominal cavity through a small orifice preferentially of 5 or 10 mm diameter under direct vision. The device is provided with a protuberant means, preferentially situated opposite to the attachment side to the cavity wall, that permit grasping and handling by the introducer. The introducer is represented by a slender instrument provided with a grasping end that can grasp the device from the protuberant means and bring the virtual port device and position it at the desired location on the interior surface of the working cavity, or onto tissue within the working cavity.

Alternatively, in case of an inflation chamber, or a vacuum device provided with a permanently attached canula, this canula may serve as an introducer means. The same introducer device may serve for changing the position of the device on the inner side of the working cavity wall, or on the tissue within this cavity. In order to do this the introducer means is introduced into the cavity through an existing opening and the virtual port device is grasped under vision by the protuberant means, the attachment means to the cavity wall, or inner tissues such as magnetic, vacuum, adhesive are released completely, or partially, the introducer means will move the virtual port device and the attachment means will be reactivated at this location and the introducer means will be detached from the virtual port device. This maneuver may be repeated as many times as is necessary.

In case the device is provided with a one way valve, or valves and with connection means to these valves, the device may be introduced in the working cavity, and manipulated as above mentioned in the previous paragraph, through the small orifice in the cavity wall by the tube or canula that are affixed to this connection means and positioned to the proper place under vision using this tube or canula means. The connector used for attaching the canula may be of a mechanical articulation type for example a bayonet connection, or by using an inflatable balloon at the end of the canula to firmly attach it to a proper cavity on the anchoring device.

In another preferred embodiment the virtual port anchoring device is attached to the inner side of the cavity by small barbs that penetrate the tissue when the device is pressed by the introducer against it. This entire device, a segment holding the barbs, or only the barbs may be manufactured of biodegradable material. This anchoring device might be shaped as a solid spherical or ellipsoidal device that can be introduced through a small diameter orifice using a detachable introducer, or it can be provided with an inflatable chamber that can be inflated with liquid or gas to a larger volume having a larger attachment surface to the inner surface of the cavity.

In this case, the introducer may be a canula permitting inflation of the chamber through a one-way valve, and being detachable attached to it. The device is released from its position by using traction with the introducer and reattached to another position by a similar maneuver. In case of using a biodegradable device or a part of the device being biodegradable, this segment can be left attached to the original place and the second component can be removed through an orifice in the cavity wall. In case of an inflation canula serving as introducer, this canula is reattached to the one-way valve of the device through a connector, and the device is detached from its location by using traction, and reattached to the new location, or removed from the cavity. The connector used for attaching the canula may be of a mechanical articulation type for example a bayonet connection, or by using an inflatable balloon at the end of the canula to firmly attach it to a proper cavity on the anchoring device.

Alternatively, the device may be attached to the undersurface of the cavity by a clip means, that is, advanced over a segment of tissue from the undersurface of the abdominal wall that is grasped or sucked by a specially designed means. Such a device may be designed as an inverse tweezers that has central passage for passing the grasping or suction means and a means for manipulating it and approximating it to the undersurface of the cavity wall.

In another embodiment the anchoring device is attached to the underside of the cavity using a wire shaped as a loop that penetrates the entire cavity wall. This anchoring device might be shaped as a solid spherical or ellipsoidal device that can be introduced through a small diameter orifice using a detachable introducer, or it can be provided with an inflatable chamber that can be inflated with liquid or gas to a larger volume having a larger attachment surface to the inner surface of the cavity.

In this case, the introducer may be a canula permitting inflation of the chamber through a one-way valve, and being detachable attached to it.

Preferably, the attachment device is shaped as an umbrella that opens on the undersurface of the cavity and is held in this position by and prevented from flipping back on itself by some reinforcing means. The increased contact surface of the anchoring device to the inner surface of the cavity may permit better fixation of the anchoring device to the cavity wall. The wire is provided at its end with a loop or other attachment means to the anchoring device, and the anchoring device is provided with a hook means for engaging the loop means of the wire. The wire may be introduced directly through the cavity wall, or through a special needle used to pierce the cavity wall.

The wire is introduced to the proper place though the cavity wall by transillumination guidance or by other imaging means. When moving the anchoring device to another position the device is detached from the wire and this wire, or another wire is introduced to the new position and the anchoring device is attached to the attachment wire using the introducer, by the same maneuver mentioned previously. These mechanical attachment means of the anchoring device are somewhat more invasive than the previously mentioned means by are much less invasive than creating orifices of 5 to 10 mm diameter in the cavity wall necessary for introduction of standard retractors and other working elements.

Gas insufflation has its potential drawbacks such as generation of positive pressure, which in case of abdominal laparoscopy can be detrimental in obese patients, patients with chronic respiratory and/or cardiac diseases. Additionally gas insufflation, necessitates an insufflator device, can result in rapid loss of the working cavity when there is a gas leak, or when the gas exhaust results in inadequate view of the surgical site.

The embodiments in which the anchoring means are held in place by some device on the outer surface of the cavity, such as by magnetic attraction or by wires piercing the entire thickness of the cavity, can serve also for gasless (atmospheric pressure) endoscopy or laparoscopy. In this case, an initial port is performed using positive pressure laparoscopy, then the attachment means are attached to the undersurface of the cavity for endoscopic retraction and for retraction of the body wall, thus serving a dual role.

The devices on the outer surface of the cavity can be attached to a frame or to rods fixed to the operating table, to the operating room floor or ceiling and serve for lifting the cavity wall, permitting to perform the intervention without the necessity to insufflate the cavity with gas.

Thus, the undesired effects of pressurizing the abdominal cavity during a surgical intervention can be avoided.

Figure 7:
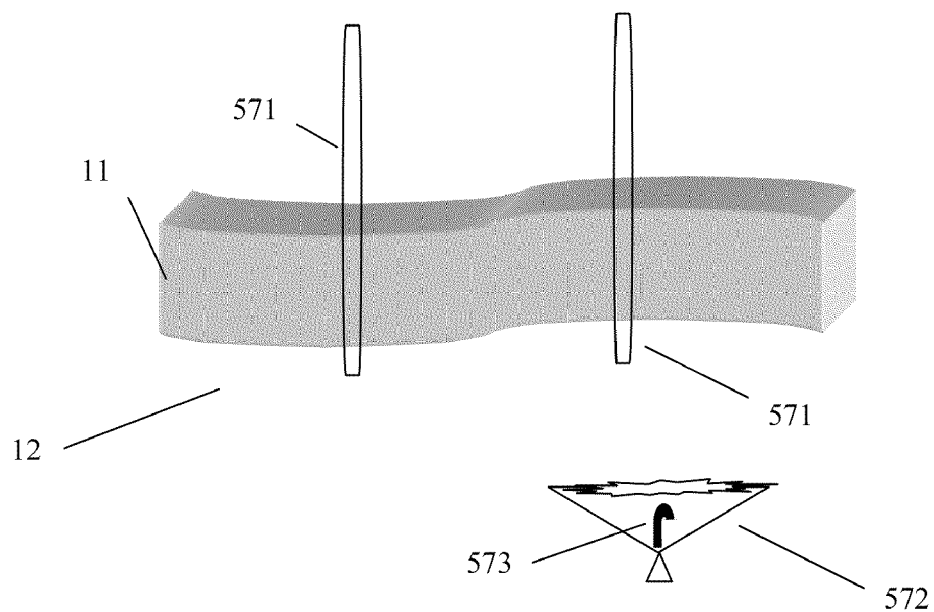

FIG. 7 details a virtual port including a wire 571 with a reversed umbrella-shaped device 572 with a hook 573, before being attached into place to abdominal wall 11.

Figure 8:
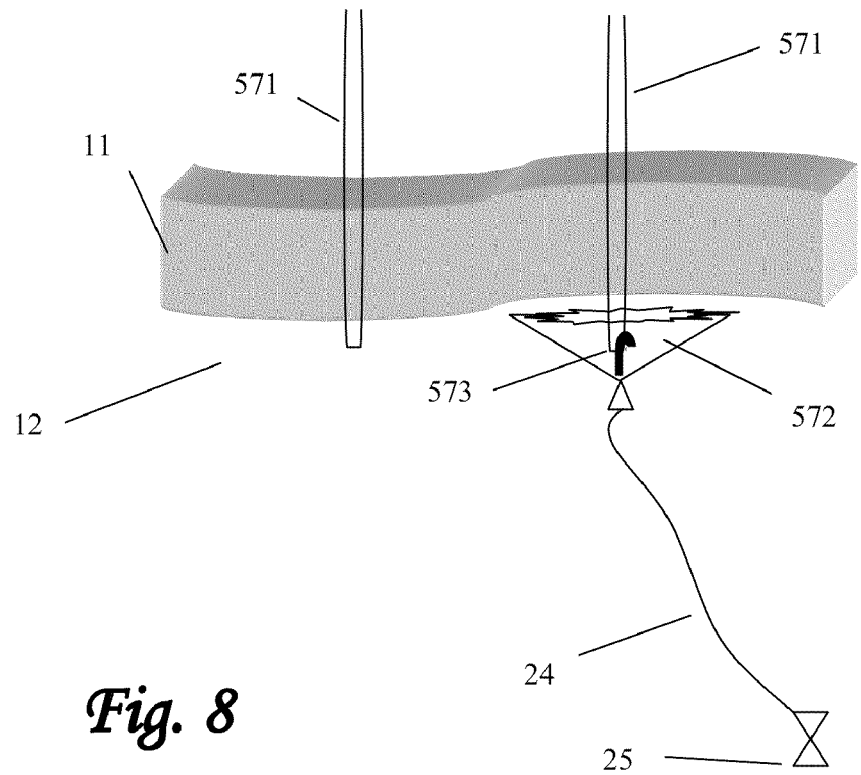

FIG. 8 details a virtual port, use of a wire with a reversed umbrella-shaped device attached into place.

Figure 10:
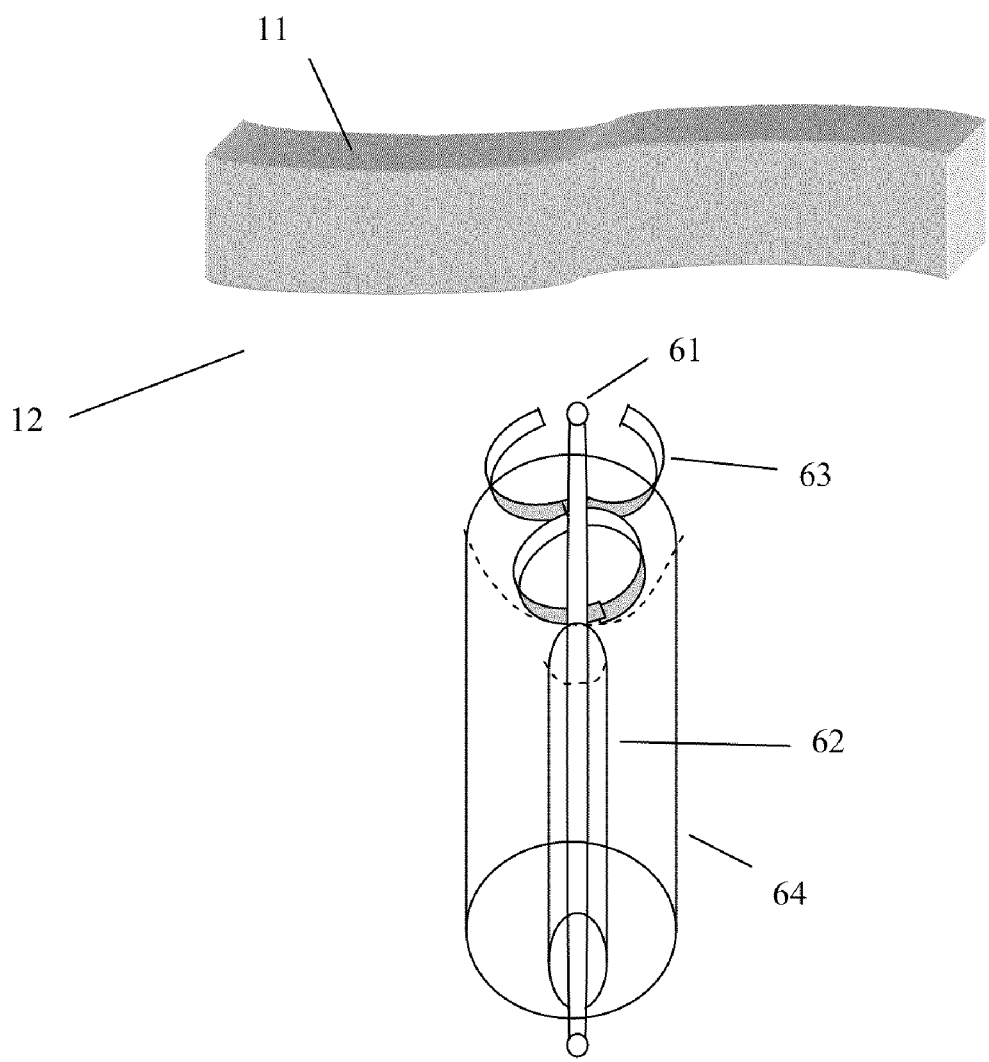

FIG. 10 details a virtual port self retaining clips, tweezers-type, including a vacuum tube 61 for pulling the abdominal wall 11 tissue, a holding tube 62 for pushing the clips means, clips means 63 in place, and outer tube 64 for closing and opening the clips means 63.

Figure 11:
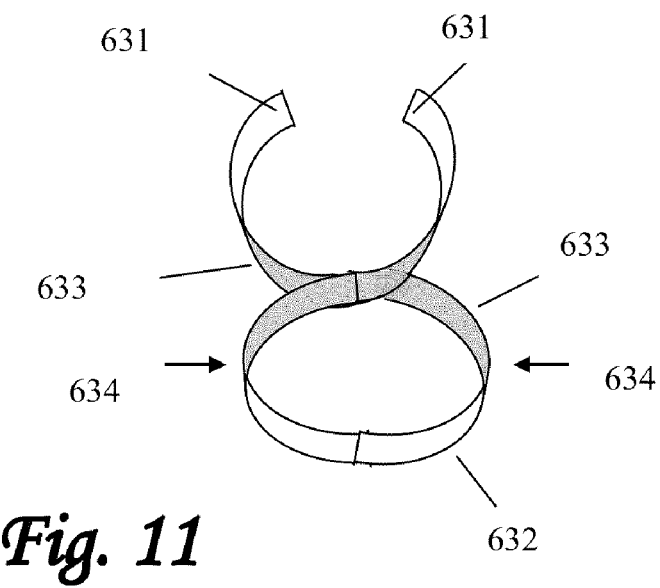

FIG. 11 details the structure of a virtual port self retaining clips.

The clips means is made of elastic wire, for example, has a pair of holding tips 631 and a wider base 632, connected through crossed arms 633.

By applying force 634 inwards opens the tips 631, such as when the base 632 is in a tube 64 when base 632 is released, then tips 631 close to hold tissue therebetween. A vacuum tube 61 may pass through the base 632.

Figure 12:
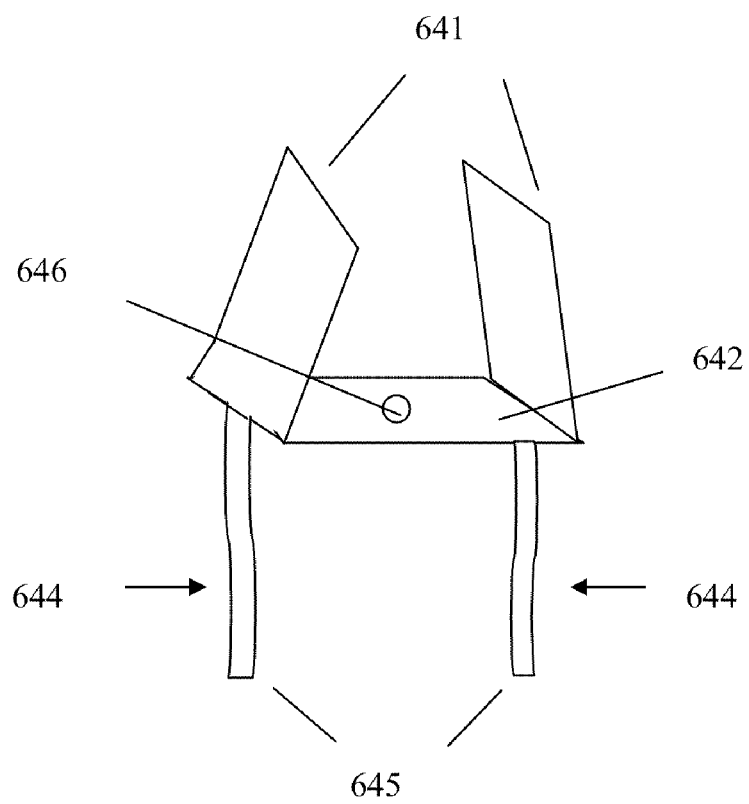

FIG. 12 details another embodiment of a virtual port self retaining clips, wherein the clips means is made of elastic ribbon example, has a pair of holding tips 641 and a base 642, such as the tips 641 are normally close to each other or in contact with each other by applying force 644 inwards on arms 645 will open the tips 641, to attach to tissue.

There may also be a hole 646 for the vacuum tube 61.

Figure 13:
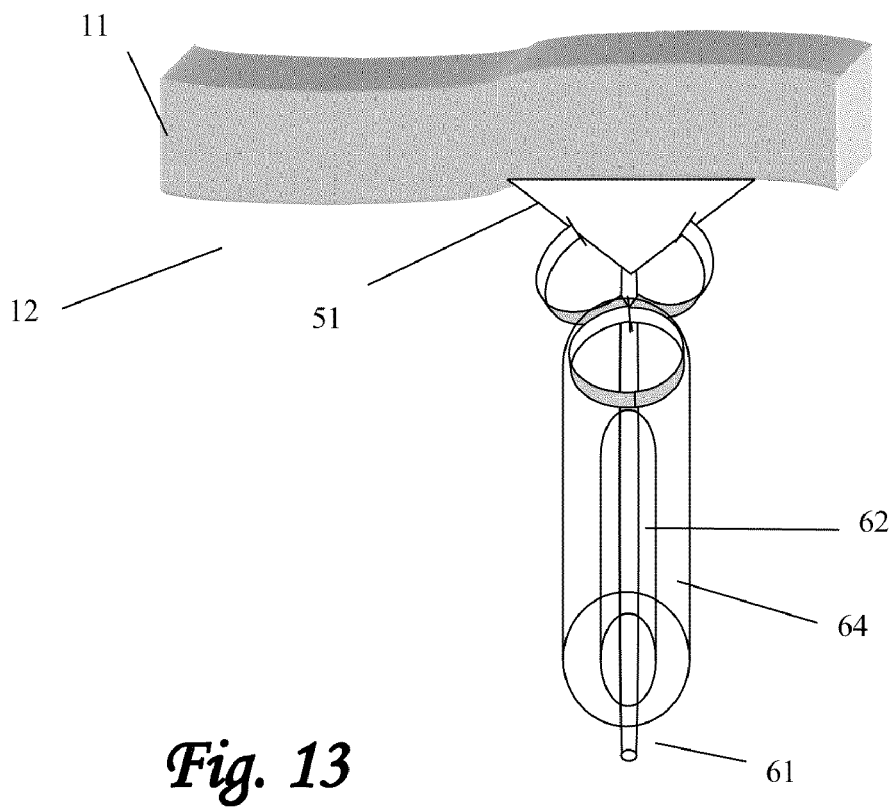

FIG. 13 details a virtual port self retaining clips with a vacuum cup/grasper means 51 using the aforementioned three tubes structure.

Figure 14:
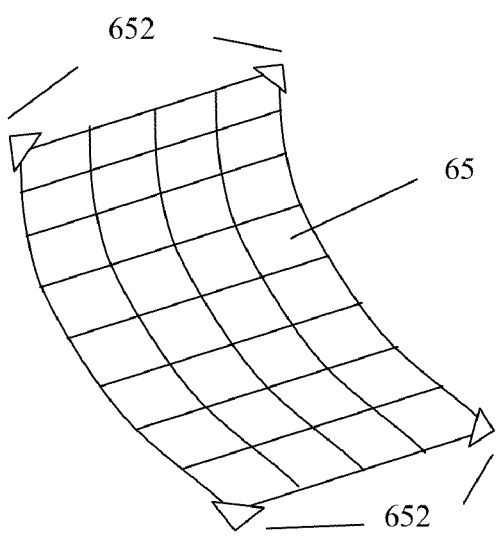
Figure 15:
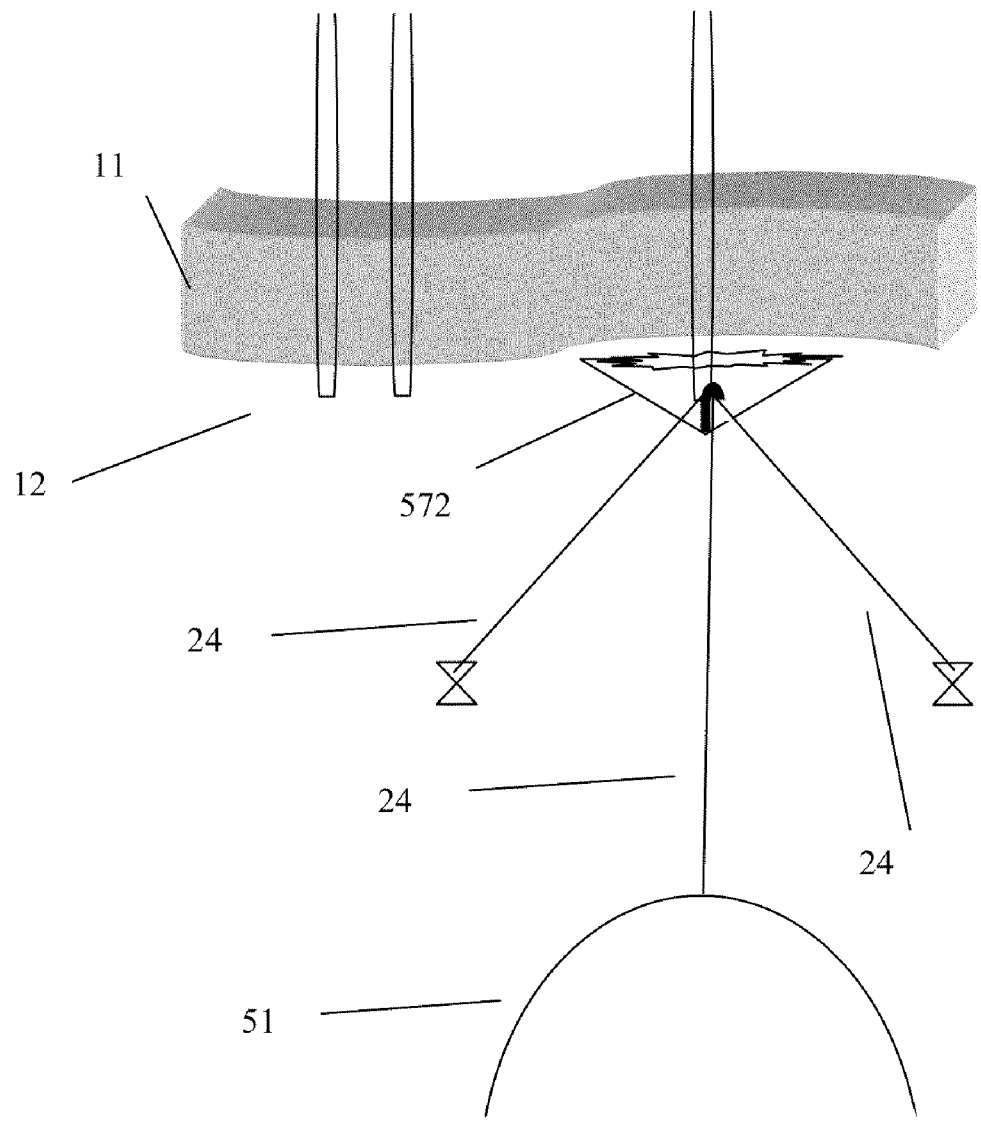

FIG. 14 details a net/mesh for holding internal organs or pushing them aside. A net 65 has a plurality of holding points 652, each can be attached to an anchoring point created using either of the structures detailed above FIG. 15 details means for holding an internal organ by attaching it to a virtual anchor point 572, and connected through a wire 24 to vacuum cup/grasper means 51 to attach to an internal organ.

Several organs can thus be secured to one anchor point, using several wires 24, each with its grasping means 25 attached thereto.

In laparoscopic procedures, the attachment means may be fixed to the undersurface of the cavity and moved from one position to another, using endoscopic instruments such as graspers under the direct vision the endoscope.

Figure 16:
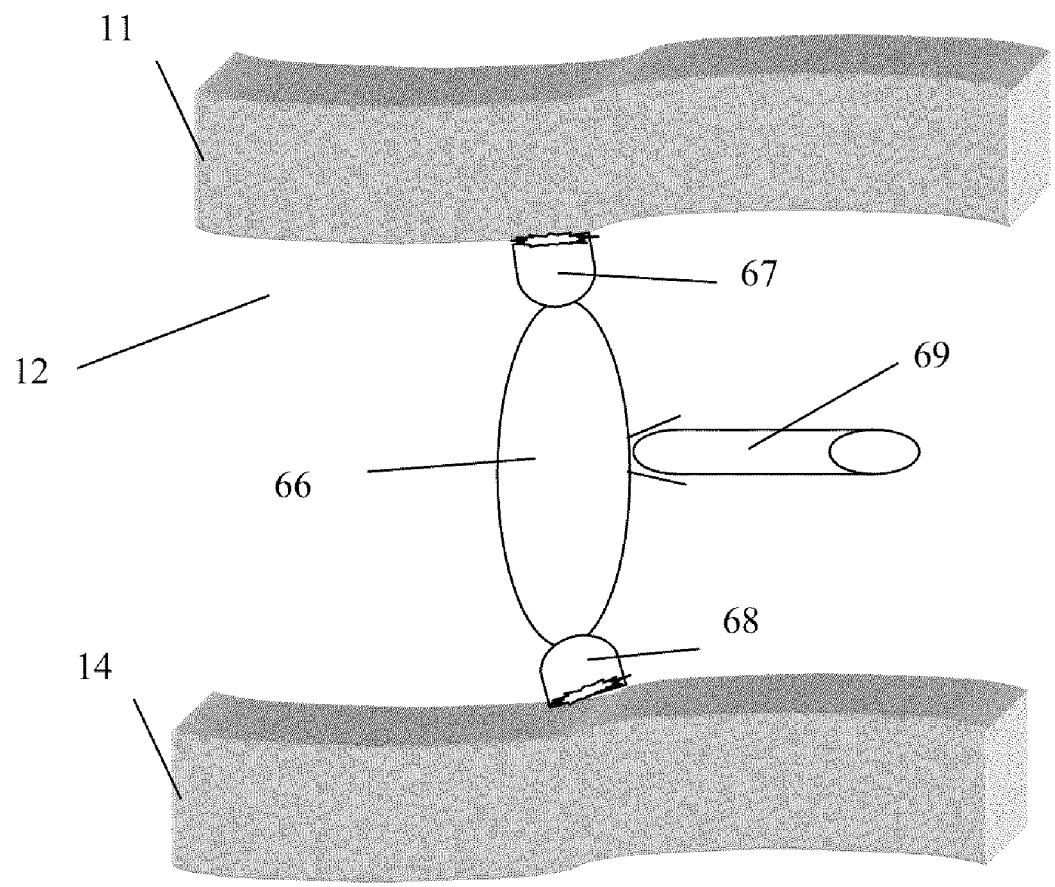

FIG. 16 details an inflatable balloon 66 with affixed virtual port devices, being secured to two cavity or abdominal walls 11, 14.

The inflatable balloon 66 may include holding means 67, 68 to attach to above walls—such as asperities on the extremities of the balloon 66, vacuum cups or any of the above means.

Furthermore, the balloon 66 may include inflating means 69, such as a tube to inflate with a fluid. When inflated, the balloon 66 may be used as a support means inside the body, or a means to move internal organs therein.

Figure 17:
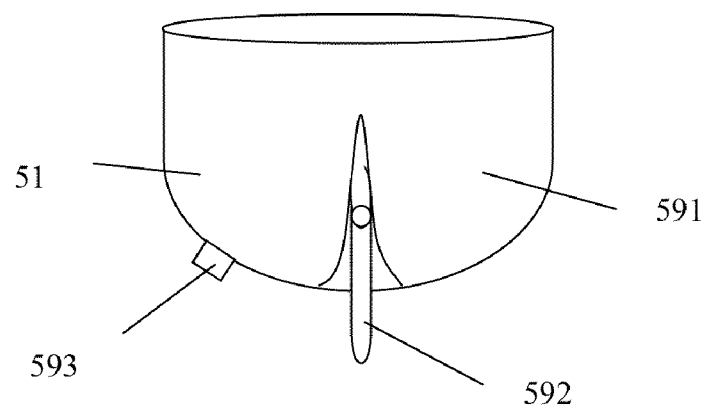

FIG. 17 details vacuum cup with a two-state valve in its closed state.

The vacuum cup 51 has a flexible valve tube 591 which is closed, and a rigid valve tube 592 partially inserted therein.

Figure 18:
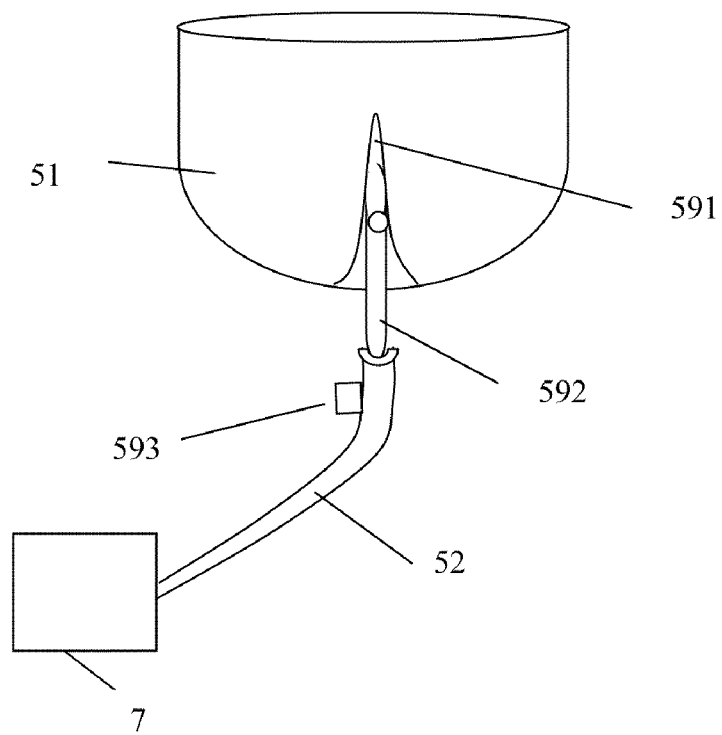

FIG. 18 details vacuum cup with a two-state valve in its Open state.

Method of operation: the valve is normally in its closed state, due to elastic action of rubber tube 591.

To create vacuum, connect to vacuum pump and press rigid tube 592 into cup, through rubber tube 591. Air is eliminated and vacuum created.

The elastic surface of cup 51 is drawn in by the vacuum, keeping the valve Open.

When vacuum inside cup 51 disappears, for example when the side of the cup 51 is lifted up, then there is no longer a vacuum to hold the valve Open, and it automatically reverts to its closed state. In this state, the cup 51 is disconnected from the vacuum pump 7. Vacuum is still supplied to the other cups in the system, cups which are connected to the same pump 7 through the common vacuum tube 52. Vacuum will not escape through the disabled cup, since the valve there has reverted to the closed state.

Figure 19:
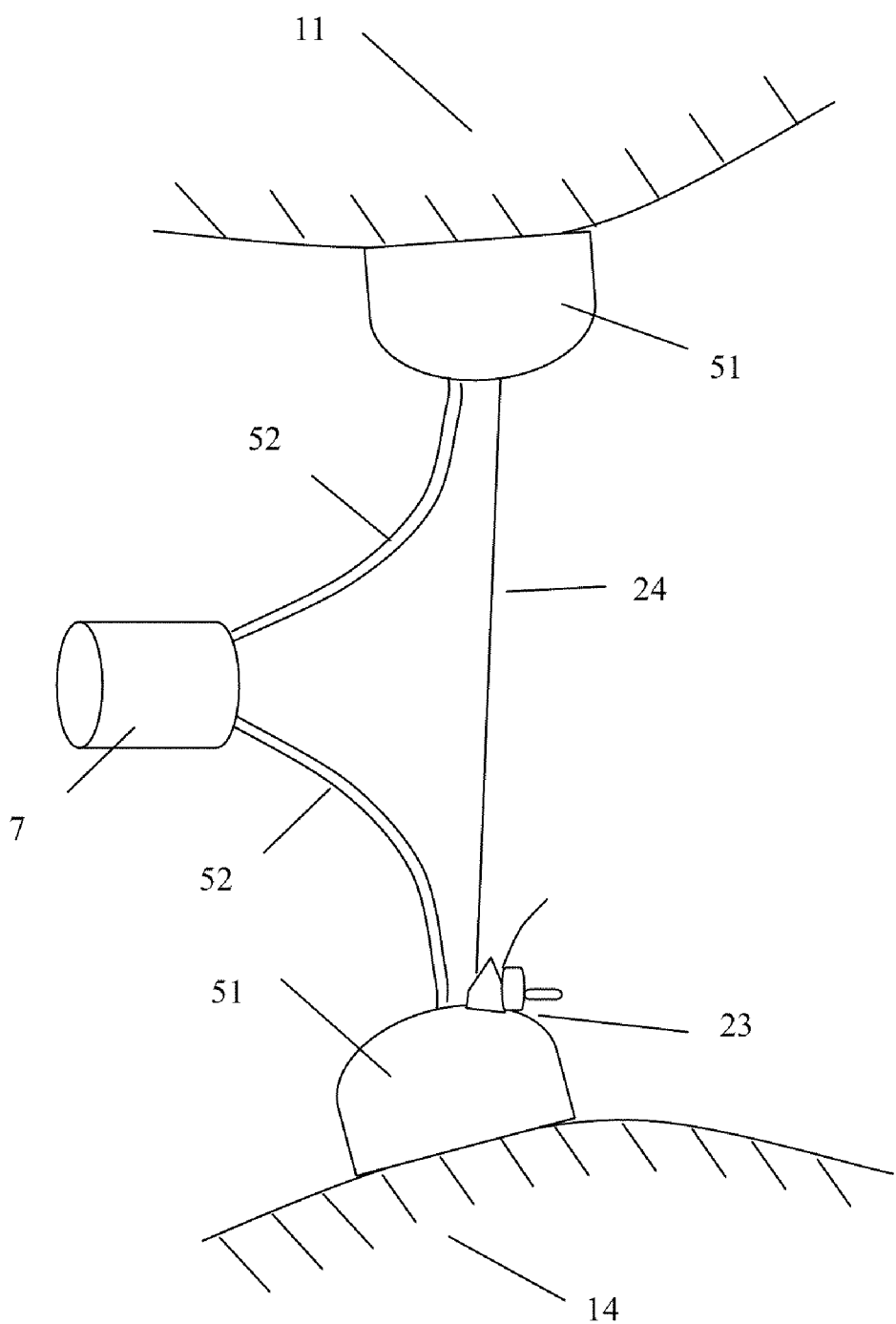
FIG. 19 illustrates a plurality of vacuum cups connected to a common vacuum pump FIG. 20 details vacuum cup with a two-state, toggle-switch activated valve in the Vacuum Activate state FIG. 21 details vacuum cup with a two-state valve in the Vacuum Preserve state FIG. 22 details vacuum cup with a three-state, switch-activated valve in the Vacuum Activate state FIG. 23 details vacuum cup with a three-state, switch activated valve in the Vacuum Preserve state FIG. 24 details vacuum cup with a three-state, switch activated valve in the Vacuum Release state

FIG. 19 illustrates a plurality of vacuum cups 51 connected to a common vacuum pump 7.

The vacuum cups 51 may be attached to cavity or abdominal walls 11, 14 and, through vacuum tubes 52, to a vacuum pump 7.

A wire 24 can be pulled to exert a force as desired by the surgeon and held in place with ratchet mechanism 23.

Figure 20:
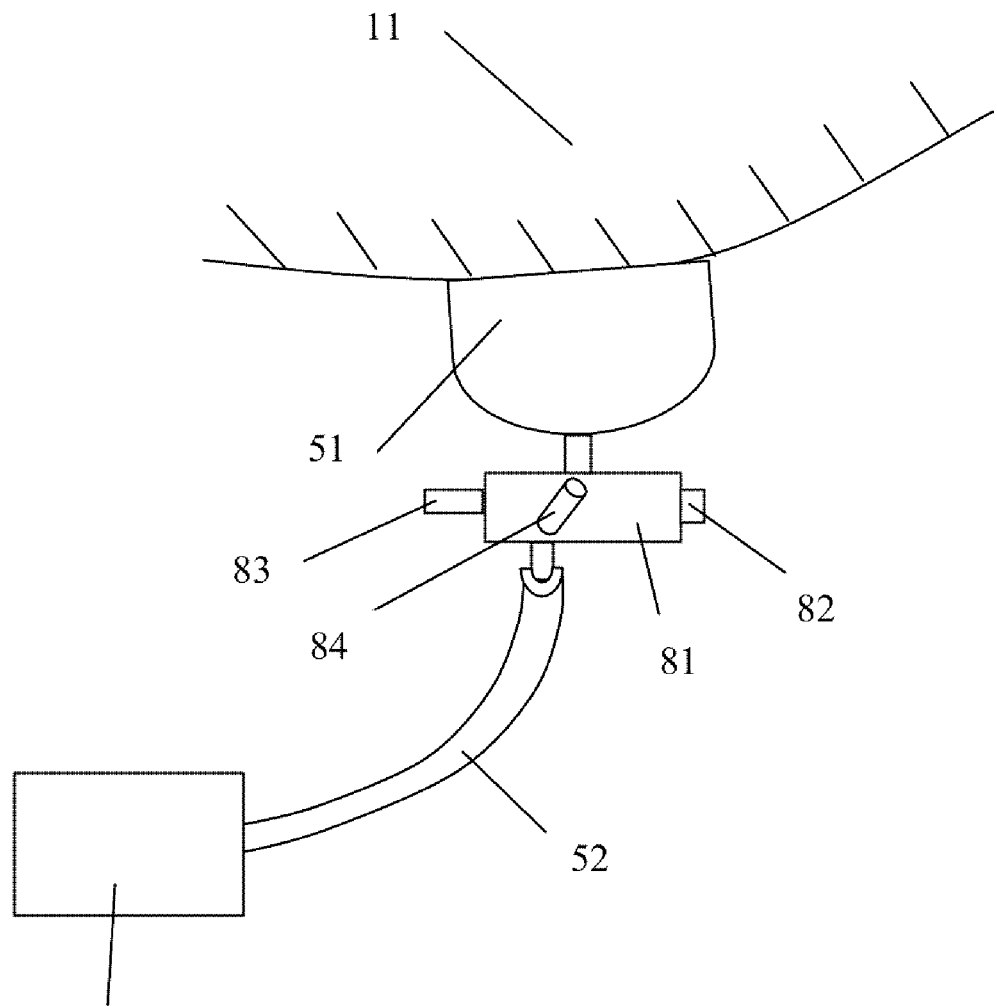

FIG. 20 details vacuum cup with a two-state, toggle-switch activated valve in the Vacuum Activate state.

This is another solution to the problem of independent control over several cups which are connected to a common vacuum pump.

Problem—when disconnected from body, to keep vacuum in tubes, as same tube is connected to several cups.

One cup can be disconnected, whilst the rest of them still operate under vacuum.

Method of use:
1. connect cup to vacuum pump using a tube.
2. open valve by pushing the Open pushbutton on the device.
3. to disconnect, press Close pushbutton then lift side lip of cup to allow air to enter.
4. If left closed—the cup can be disconnected from pump but retains its vacuum.

The vacuum cup 51 is attached to cavity or abdominal wall 11 and, through vacuum tube 52, to a vacuum pump 7.

The valve 81 is illustrated with Vacuum Activate button 82 in depressed state. The air passage 84 is then open from cup 51 to pump 7, whereas the Close Cup button 83 is inactive.

Figure 21:
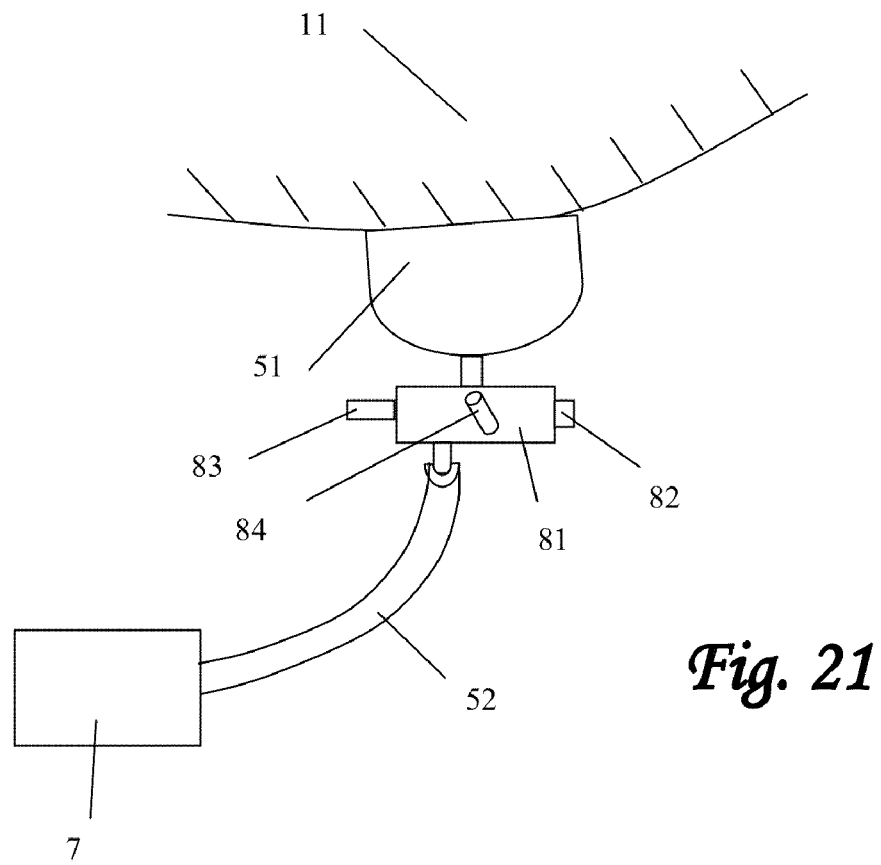

FIG. 21 details vacuum cup with a two-state valve in the Vacuum Preserve state. In this state, the Close Cup button 83 is in depressed state, and the Vacuum Activate button 82 is inactive. In this state, the air passage 84 is blocked, preventing air flow between cup 51 and pump 7 through the vacuum tube 52.

In this state, the valve 81 is closed, and preserves the vacuum in cup 51 even if the pump 7 is deactivated or disconnected.

If cup 51 is disconnected, and there is no more vacuum therein, this will not affect the performance of pump 7, which may supply vacuum to other cups which may be connected to the same tube 52.

Air will not penetrate the tube 52, since the valve 81 is closed.

Figure 22:
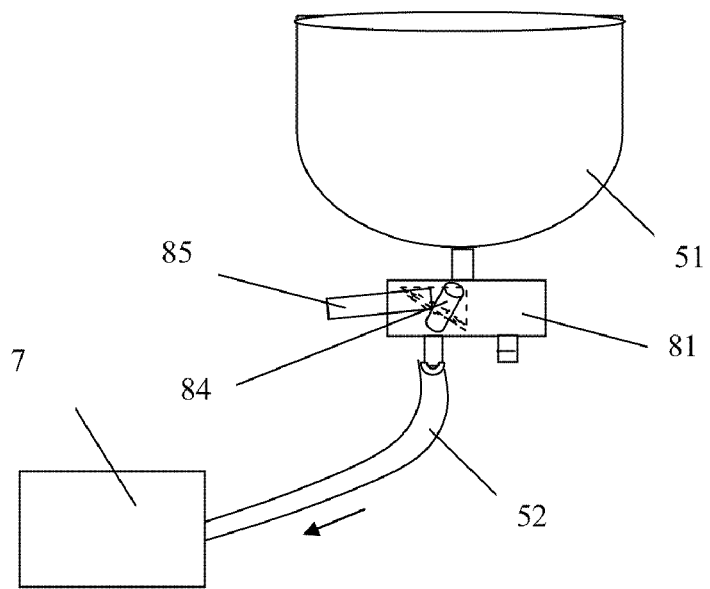

FIG. 22 details vacuum cup with a three-state, switch-activated valve in the Vacuum Activate state.

The three states include:
1. Vacuum Activate, to connect cup to vacuum pump to generate vacuum in the pump to attach it to an internal body organ;
2. Vacuum Preserve, valve closed and vacuum preserved in the cup;
3. Vacuum Release, opening a path for air or fluid to enter the cup from the surroundings.

Problem—when disconnected from body, how to keep vacuum in tubes, as same tube is connected to several cups. One cup can be disconnected, whilst the rest of them still operate under vacuum.

Also—how to release the cup without applying force thereon.

Solution: a control lever 85 is rotated into a position so as to orient the air passage 84 towards the vacuum tube 52, connecting it to the pump 7.

In this state, the valve is open, allowing the pump 7 to create vacuum in the cup 51.

Figure 23:
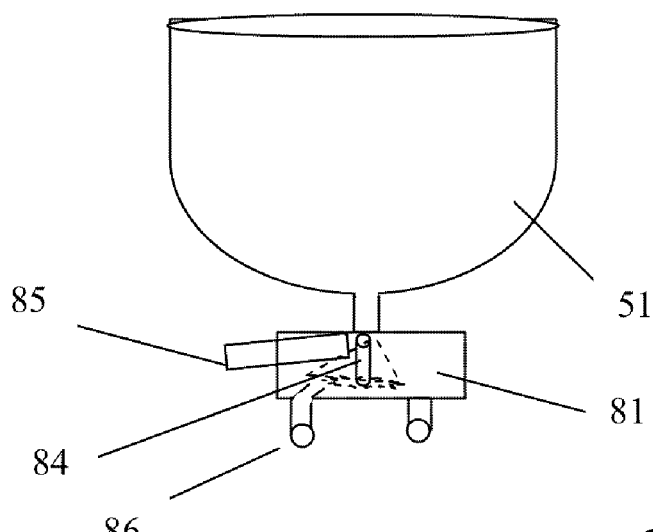

FIG. 23 details vacuum cup with a three-state switch activated valve in the Vacuum Preserve state.

The control lever 85 is rotated into a position so as to orient the air passage 84 towards a wall or block in the device.

The valve 81 is blocked, preventing air flow between cup 51 and vacuum pump or the ambient.

In this state, the valve 81 is closed, and preserves the vacuum in cup 51 even if the pump 7 is deactivated or disconnected.

The outlet 86 to the vacuum pump is blocked, so as not to disturb the vacuum to other cups, even if there is no more vacuum in cup 51.

Figure 24:
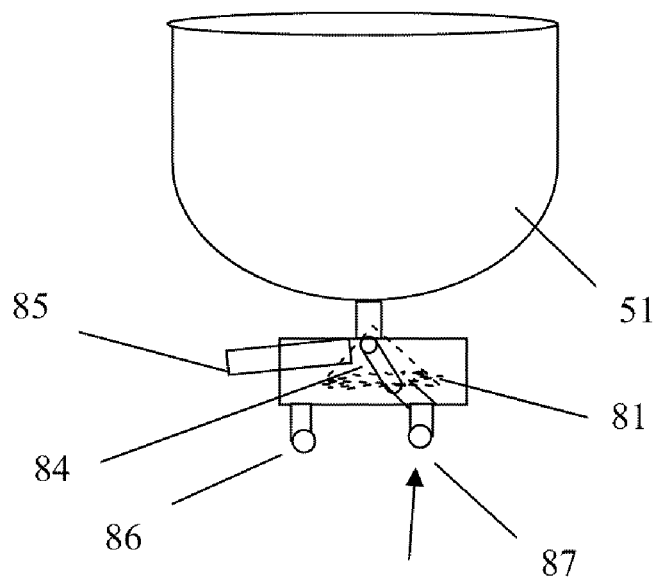

FIG. 24 details vacuum cup with a three-state switch activated valve in the Vacuum Release state.

The control lever 85 is rotated into a position so as to orient the air passage 84 towards an outlet 87 which is open to the ambient air, or air in the abdominal cavity.

Air from the ambient enters the cup 51 and cancels the vacuum therein.

The outlet 86 to the vacuum pump remains blocked, so as not to disturb the vacuum to other cups, even if there is no more vacuum in cup 51.

Figure 25:
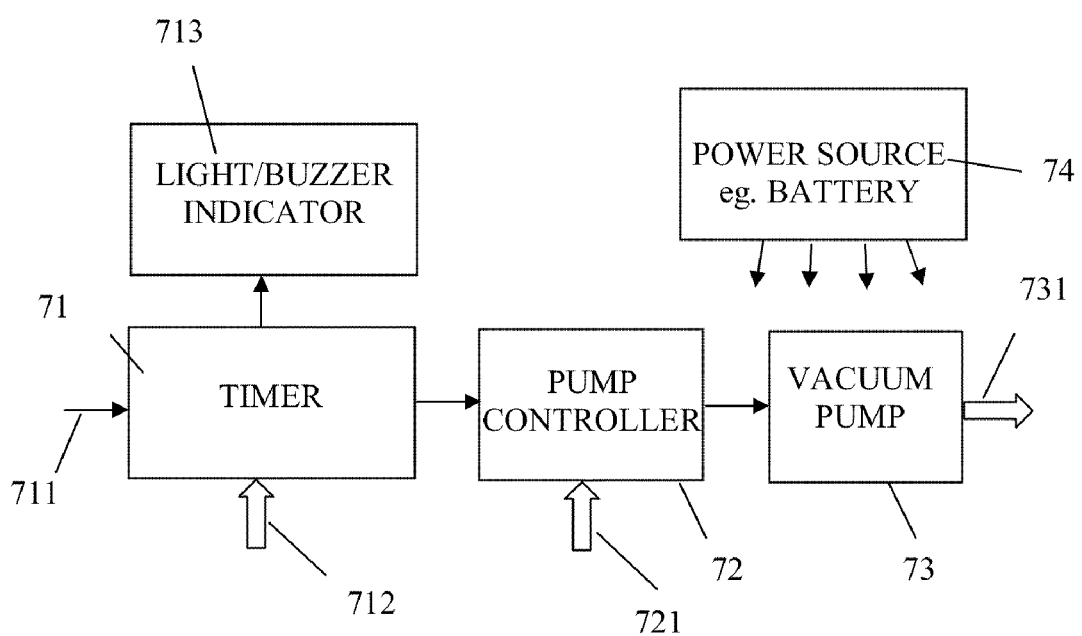
FIG. 25 illustrates an electronically-controlled vacuum pump 7

FIG. 25 illustrates an electronically-controlled vacuum pump 7.

Problem—to generate vacuum for a predefined time period, then to stop it, so as not to damage internal body organs.

Solution: A timer 71, activates pump for a predefined time interval when receiving a trigger input 711, for example pushing a button there.

The optional time interval setting input 712 may be used to set that interval.

When the time interval is about to end, or a predefined time before that, an indicator 713 indicates to the surgeon that the vacuum is about to end. The indicator 713 may include a light or a buzzer or a combination thereof, for example.

A pump controller 72 controls the vacuum level as desired, optionally according to a vacuum control input 721 settings. The vacuum pump 73 itself generates the desired vacuum, for the time period as desired, at outlet 731. A battery 74 generates the electrical power for the device.

Figure 26:
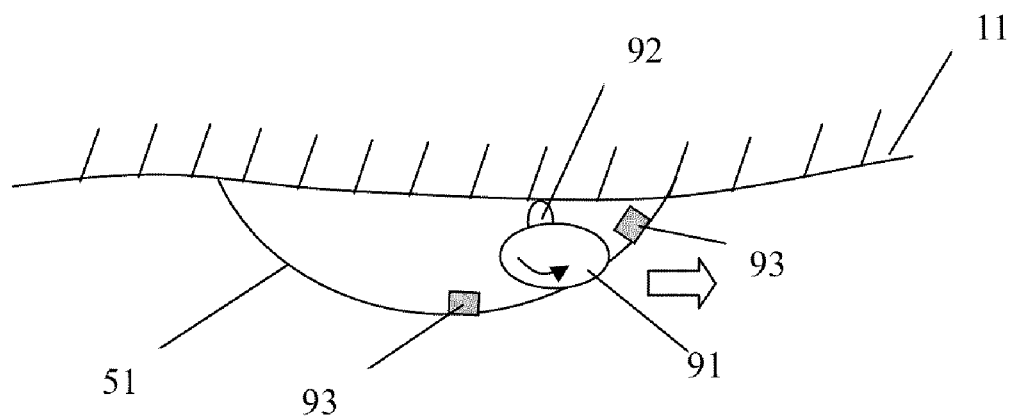
FIG. 26 illustrates a cup-moving means with partial vacuum reduction

FIG. 26 illustrates a cup-moving means with partial vacuum reduction, using a metallic ball 91 with an obstruction 92, which is rotated by means of coils 93, for generating a rotating magnetic field, to rotate the ball 91.

As the ball 91 is rotated according to external commands from the surgeon, the cup 51 is pulled sideways in the desired direction.

A partial reduction in the vacuum level may facilitate the movement of the cup 51, which remains attached to the abdominal wall 11.

Figure 27:
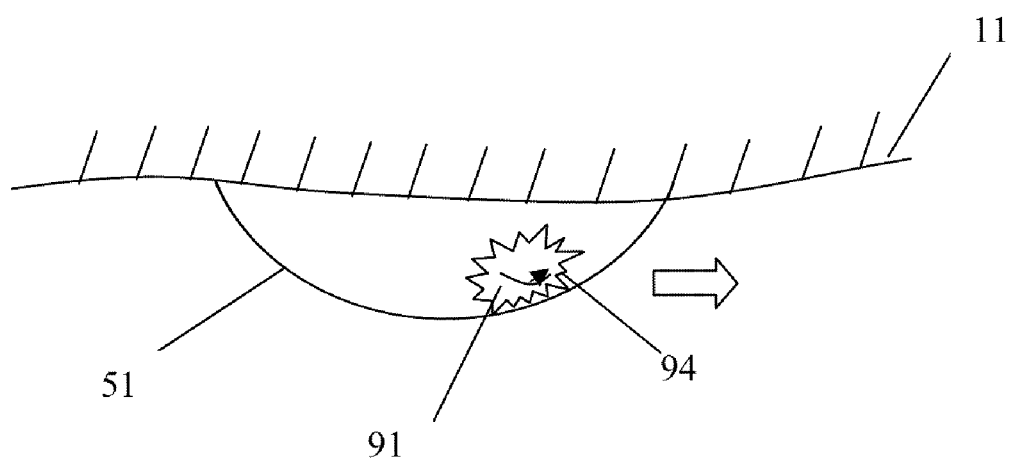
FIG. 27 illustrates another cup-moving means with partial vacuum reduction

FIG. 27 illustrates another cup-moving means with partial vacuum reduction, including a metallic ball 91 with asperities/teeth 94 on its outer surface, which allows to move the cup 51 as the ball is rotated on the tissue 11 the cup 51 is attached to.

Various embodiments of the present invention may be implemented. For example, in FIGS. 17 and 18, the valve may further include means for releasing the vacuum in the cup 51 whenever the surgeon finds this necessary, using laparoscopic tools.

Laparoscopic tools allow pushing and pinching various means in the cup 51.

Accordingly, release means are installed on the cup 51 or the tube 592 or the tube 52, allowing to open the cup to the ambient. The release means may be implemented for example using a flexible part 593 normally covering an opening there.

In the normal or rest state, there is overlap between two parts, such that ambient air or fluid cannot penetrate into the cup 51.

When pressed and/or deformed by the surgeon, part 593 allows air or ambient fluid to enter the cup 51, to cancel the vacuum within the cup. This releases the cup 51 and detaches it from the surface it has been attached to by means of the vacuum therein.

In FIGS. 17 and 18, the valve may have a structure including means for performing as follows:
a. Vacuum is formed in the cup 51 by air suction through tube 592;
b. whilst there is vacuum in the cup 51, the valve holds itself open by a deformation in its outer shape, thus keeping the rigid tube 592 within the flexible tube 591;
c. when there is no longer vacuum within the cup 51, the valve automatically shuts itself, for example by the cup returning to its normal rest shape and/or releasing the rigid tube 592 out of the flexible tube 591;
d. vacuum release means, implemented for example using a flexible part 593 which when pressed, allows air or ambient fluid to enter the cup 51, to cancel the vacuum within the cup. This releases the cup 51 and detaches it from the surface it has been attached to by means of the vacuum therein.

The above description details the use of one cup as a virtual port, or support for holding internal organs during an operation. When the surgeon desires to apply a larger force, or to hold larger organs, it is possible to use several cups. This also helps to share the force among several locations within the body, or over a larger area.

In this embodiment, several cups are attached to an internal wall of the body, for example the abdominal cavity. Each cup may be attached using vacuum and/or magnetic force. The cups may be connected together using wires or a solid plate. The plate may be either rigid or flexible, as the need be. The cups thus connected are then used to support the weight as desired or to apply the required force.

Figure 28:
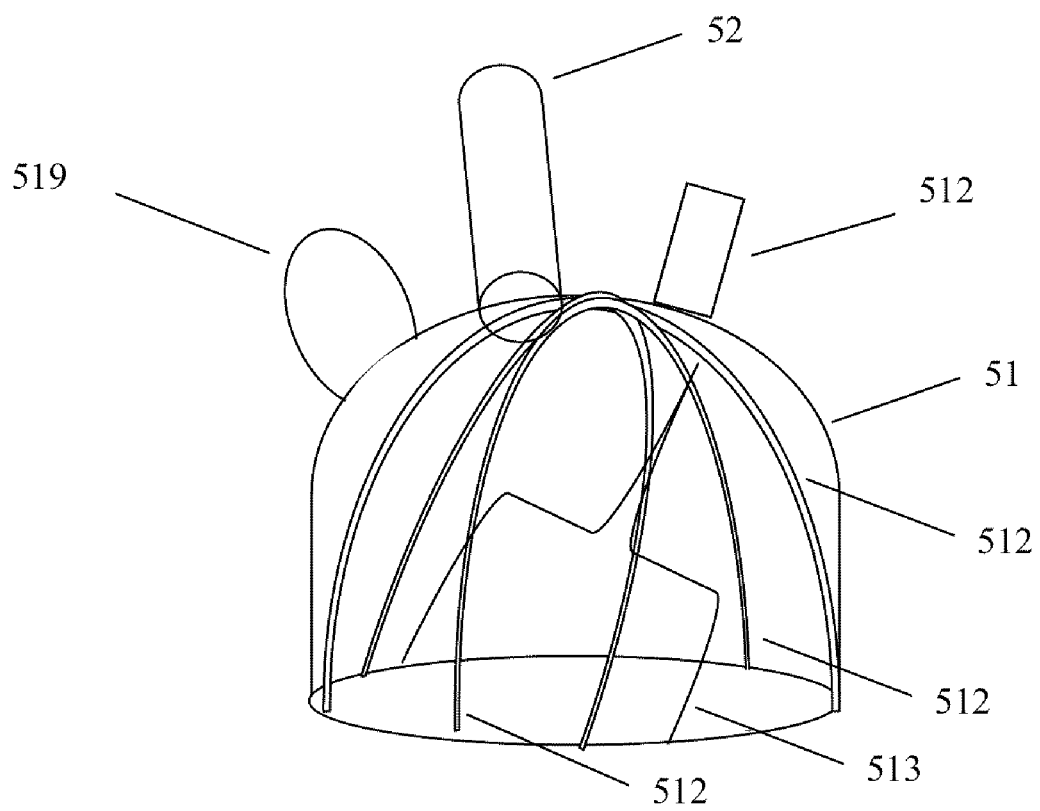
FIG. 28 illustrates the structure of a reinforced vacuum cup

FIG. 28 illustrates the structure of a reinforced vacuum cup. The vacuum cup 51 may be attached to a vacuum tube 52. The cup 51 may include internal rigid or semi-rigid ribs 512, pushing its surface to open up into a cup shape. The internal spring 513 may be connected to the ribs 512 for added strength, and to make it a foldable structure—thus the cup 51 has a superior mechanical strength and a tendency to open to its cup-like shape, and also can be folded down to a narrow shape to be inserted easily into the body, through a sleeve in the abdominal wall, for example.

The above ribs and spring ensure that the cup 51 will open up when out of the sleeve, inside the patient's body.

Thus is achieved the elastic or non-elastic cup 51, having a novel structure, which includes an internal spring 513 to open it.

The cup 51 may have stiffening ribs 512, to keep it from collapsing and improve the rigidity of the cup.

The abovedetailed cup may be inserted into a cannula of 9 mm or 20 mm (millimeters) diameter.

It may be used with a retractor or surgery-related working elements.

Mechanical attachment means 519 may be used to hold the cup by the surgeon, in order to bring the cup to a desired location or to remove it therefrom.

Attachment means 518 may be used to attach to other surgical devices using a hook/loop connection for example. Thus one part can snap on to another for a fast, strong and reliable attachment of parts and/or instruments during surgery.

Figure 29:
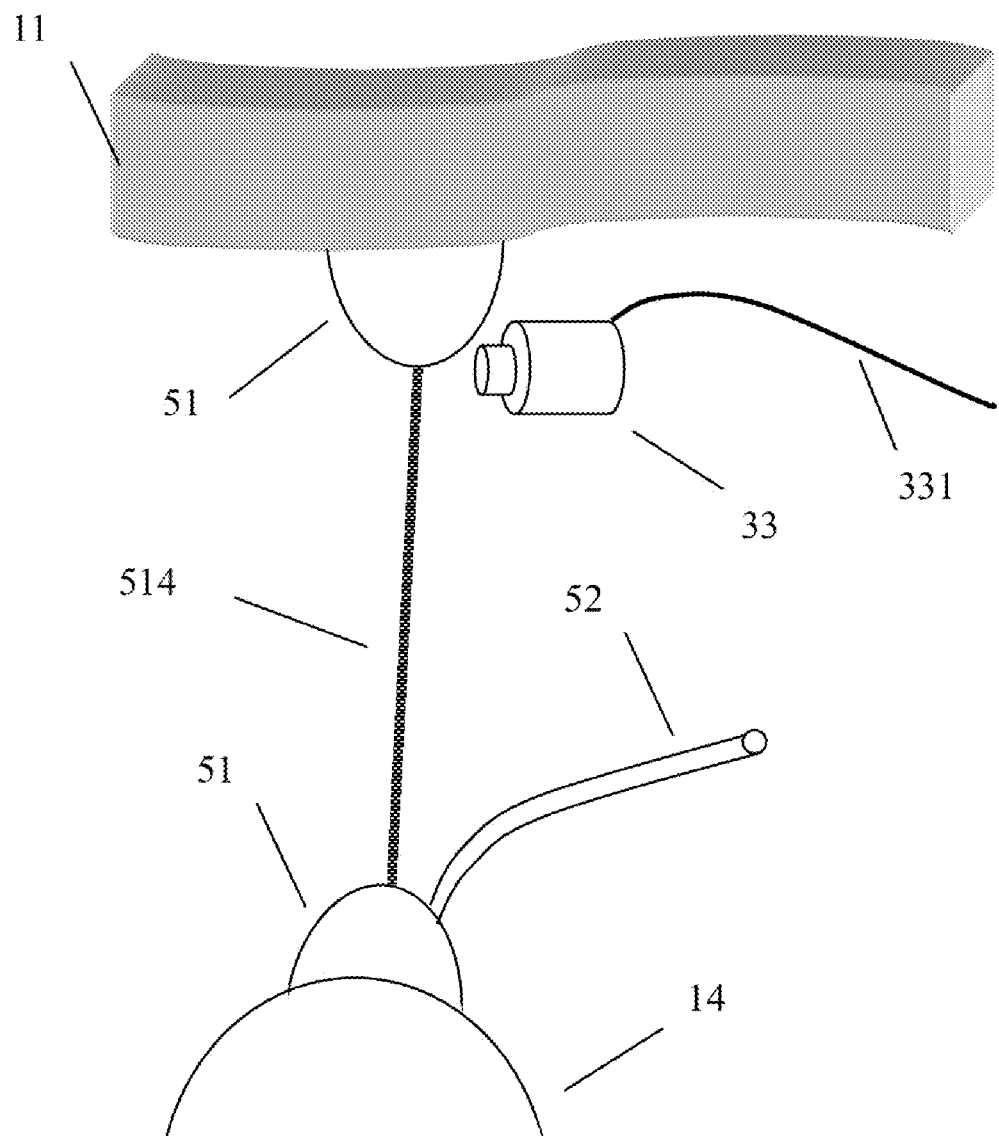
FIG. 29 illustrates the use of virtual ports

FIG. 29 illustrates the use of virtual ports A first vacuum cup 51 is attached to the cavity or abdominal wall 11, and to a vacuum/suction tube 52.

A second vacuum cup 51 attached to an internal organ 14, with mechanical coupling 514, such as a rigid or semi-rigid strip, between the above cups.

A TV camera 33 may also be installed, connected to a TV camera 331 cable.

Figure 30A:
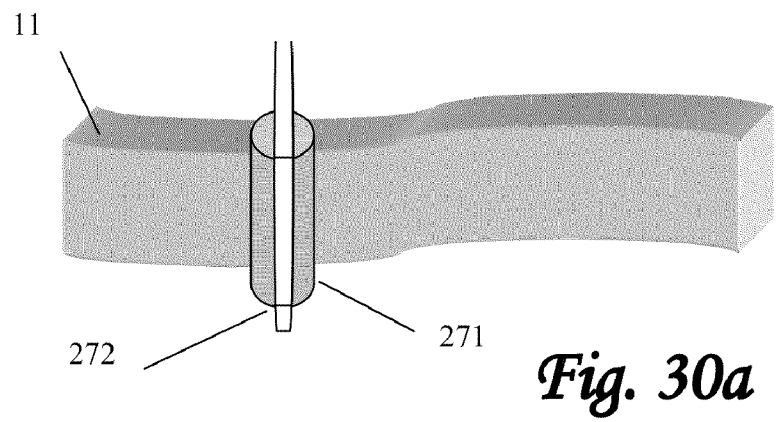
FIG. 30A details the insertion of a hollow needle through the cavity or abdominal wall FIG. 30B details the insertion of a surgical device FIG. 30C details the attachment of a surgical device to the virtual port.
Figure 30B:
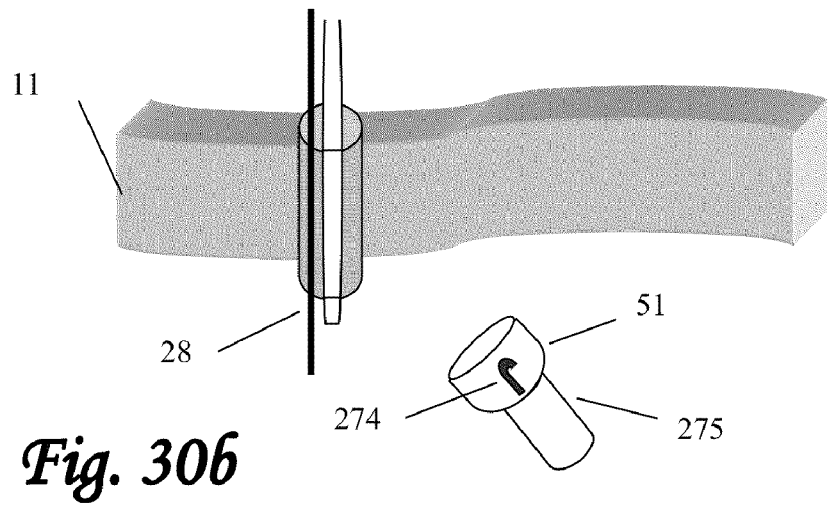
Figure 30C:
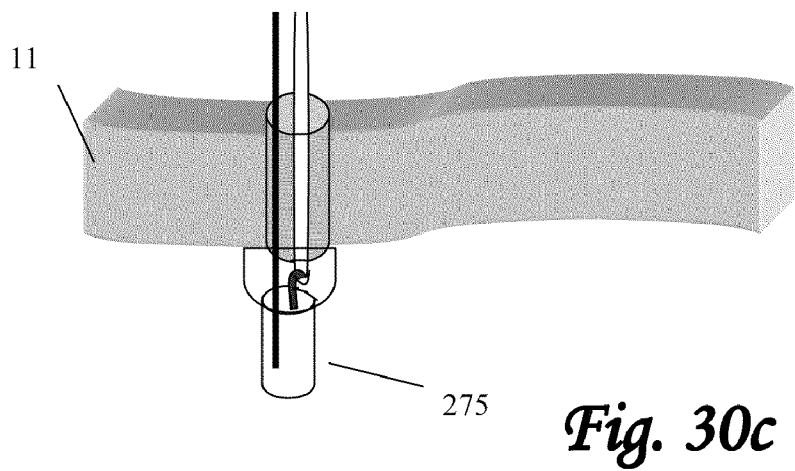

FIGS. 30A, 30B and 30C detail the structure and operation of another embodiment of a virtual port, used for working instruments.

In this embodiment, the virtual port instrument may serve for attaching various instruments such as scissors, dissectors, clippers, staplers, needle holders etc. These working instruments may be flexible, or articulated and are introduced through an opening in the cavity wall and their shaft is attached to the virtual port device, which acts like a hinge for remote manipulation of these instruments.

The anchoring device may serve also for anchoring and as a hinge for flexible, or articulated working instruments, such as graspers, dissector, clippers, cutting and hemostatic instruments, needle holders, etc. The shaft of these devices is attached to the device before its introduction within the working cavity.

Alternatively, a special sheath or sleeve is attached to the virtual port device, which permits the introduction of the working elements through this sheath and also permits interchange of such instruments after removably affixing the virtual port device to the inner side of the cavity wall or on the tissue within the working cavity.

The device includes means for attaching various retractors or surgical working instruments such as scissors, dissectors, clippers, staplers, needle holders, etc.

The new structure of the device includes, inter alia, its antenna-like shape, a telescopic element with an internal spring. It attaches to loop using hook connected to it, with a rod being inserted into telescoping element.

Through the sleeve, the surgeon may insert working element such as catheter.

The element is attached to the lower end of the telescopic element.

FIG. 30A details the insertion of a hollow needle through the cavity or abdominal wall 11. It uses just a small hole in the wall 11, so as not to leave a visible scar.

This procedure and device sets a virtual port in that location, which can subsequently be used to secure various surgical instruments in that place.

A loop is inserted through the needle into the abdominal cavity a narrow, rigid rod is inserted as well—for example a steel rod of about 2 mm thickness.

FIG. 30B—a surgical device is inserted into the body through a larger hole, for example through the navel using a sleeve. It has a hook and a cup. It is brought to the virtual port.

Preferably, it has a hollow structure, with a central longitudinal hole.

The part 275 is preferably a telescoping element, which can be expanded against an internal spring therein.

FIG. 30C—the hook is attached to the loop. The loop is pulled out from the outside, thus attaching the device to the wall 11 and securing it into place.

The narrow, rigid rod 28 is inserted into the longitudinal hole of device 275.

The total result is that the instrument 275 is now secured to the location of the virtual port, and can be manipulated by the surgeon from the outside, using for example a steel rod 28 of about 2 mm thickness.

The device 275 has a hollow structure, with a central longitudinal hole.

Preferably the hole is not circular but asymmetrical, rectangular for example, with rod 28 having a corresponding shape.

This will prevent free rotation of the instrument 275 with respect to the manipulating rod 28. This allows the surgeon to better control the instrument, to manipulate it in three dimensions, including rotation about its axis.

Figure 31:
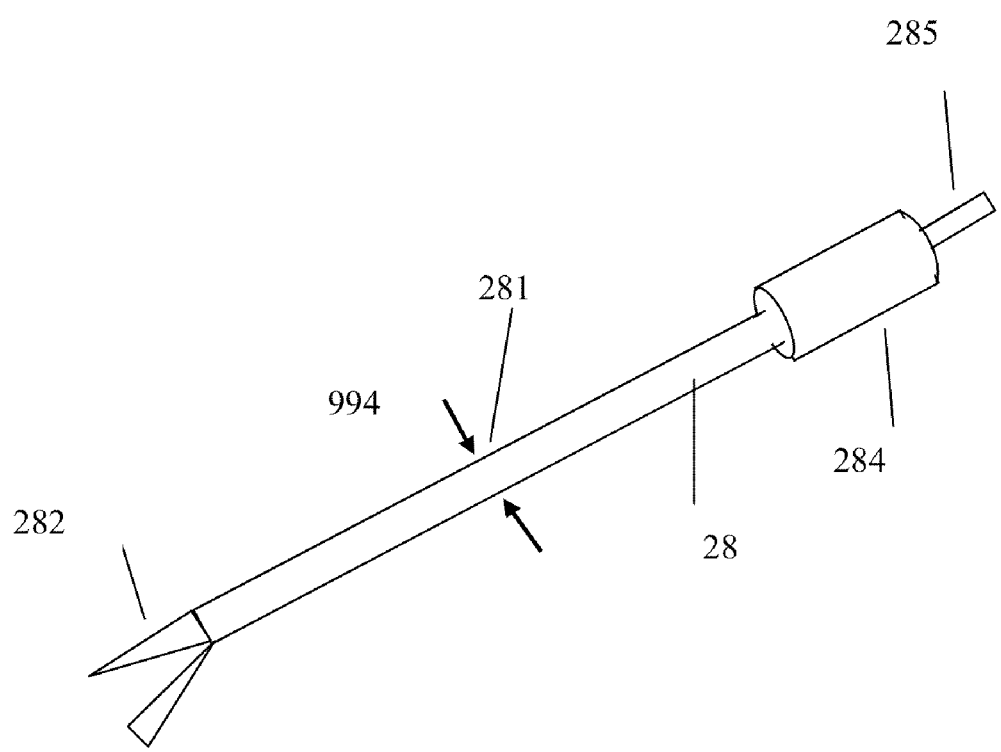
FIG. 31 details a rod for manipulating surgical tools.

FIG. 31 details a rod 28 which may include, at its end, means 282 for attaching it to the instrument 275, or surgical working element means. The total thickness may be about 4 mm. At its other end, the rod 28 may include a handle 284 for the surgeon, and/or means 285 for connecting it to a central motorized station 117.

This connection allows the movements of rod 28, and the surgical tool connected thereto, to be controlled by small motors rather than manually.

Preferably the rod 28 is thinner throughout its length except for its ends, for example at location 281 its thickness being about 2 mm.

The novel innovative concept herein discloses allows for various embodiments in a modular structure. It covers various systems, from the simple to the complex.

A simple system includes retractor for manual surgery, using a small opening in the abdominal wall. A more complex system uses motors, is more comfortable to the surgeon and uses 3D display, with several TV cameras.

The cameras may be RF and/or IR. The precise, known location of cameras allows to compute distances inside the body and the precise location of items in the surgery arena.

The system uses small diameter holes in the abdominal wall for the virtual ports locations 114, of 1-2 mm diameter each, and one larger hole 113 for inserting instruments, about 5-10 mm diameter, in the patient's navel for example.

The hole in the navel causes less pain and is practically invisible if in the range of about 5-10 mm in diameter.

This allows easy insertion, replacement of surgical instruments through a sleeve 116 in the larger diameter hole 113.

Figure 32:
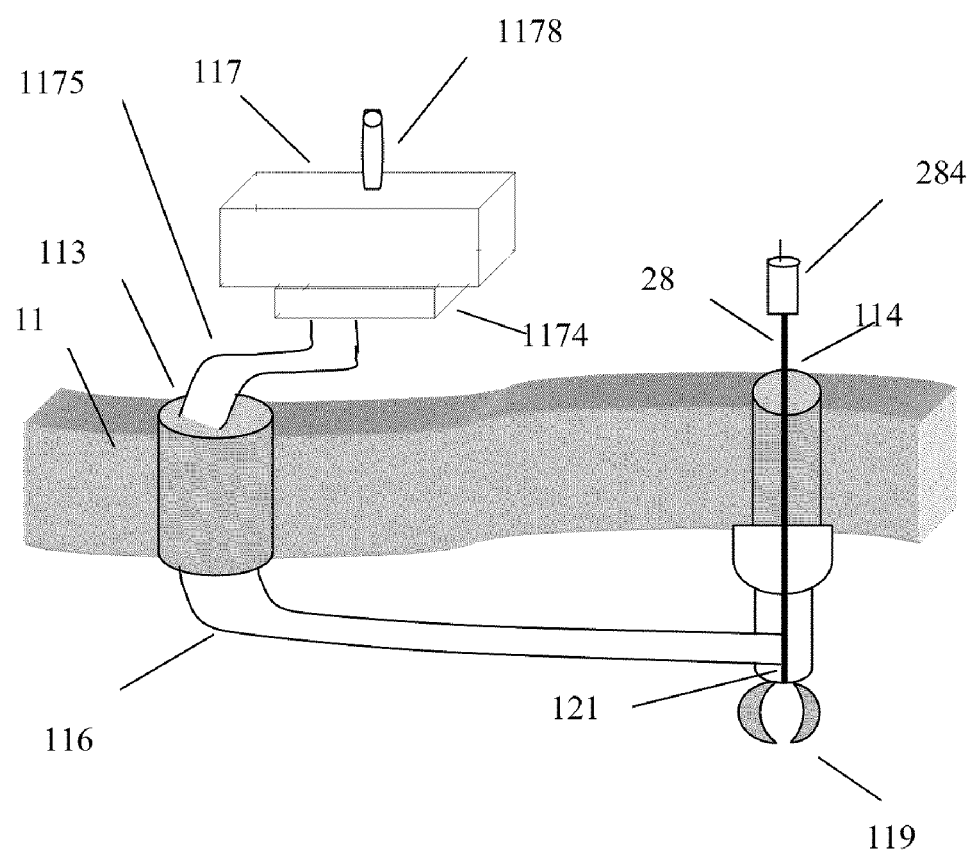
FIG. 32 details a motorized/manual surgery support system.

FIG. 32 details a motorized/manual surgery support system.

This is a simple, low cost embodiment of the inventions, offering various benefits.

Surgical tools may be inserted through an opening 113 and a sleeve 116.

One end of the sleeve 116 is secured to the opening 113 in the abdominal wall 11, and its other end is secured to the virtual port at location 114. Thus, a plurality of tools can be inserted into the patient's body and brought to the precise surgery site at location 114.

The surgery site may be changed at short notice as the need be, by creating a second, third, etc. site 114 as detailed above.

The surgical tool 121 is manipulated by the rod 28 in two or three dimensions. Additionally, the end of the tool and its other options may be controlled by the central motorized station 117.

Station 117 may include one or more small motors, preferably DC servomotors. Mechanical motion is transferred through flexible means 1175 and coupler 1174 to the surgical tool 121.

The control site 117 may include a control joystick 1178, to control it in three dimensions (3D), 4D or 6D. The unit 117 allows all the surgical movements as required.

It is a small device, about 5-7 cm size, including small motors, preferably electrical servomotors. The movement of the motors is controlled from one place. The device may include other force generating means as known in the art, including but not limited to solenoids, hydraulic and/or pneumatic means.

This structure allows complete control over the surgery element or elements, from one central control site or desk 117, preferably using a joystick.

The movement transfer means 1175 may allow movement in three dimensions, transferring movement from small motors external to the body. In this example, the motor movement is converted into a movement of forceps 119 internal to the body.

The rotation of surgical device 119 is also possible, then 4 degrees of freedom are achieved 4D.

Benefit—just a small hole, for example about 1-2 mm diameter at location 114, versus a several centimeters diameter hole in prior art.

Preferably a hole in the navel 113—is practically invisible after the surgery, does not leave an inconvenient visible scar.

The flexible instrument 121 may be a catheter, at its end a scissors.

Benefit—surgeon can use scissors or another working element, by attaching it to the instrument and manipulating it in 4D, using an element or stick 28.

The main hole 113, of about 5-10 mm diameter, is preferably performed in the navel—it does not leave a scar.

Through this hole, a sleeve 116 is inserted.

The sleeve connects to a loop and rod near the small hole 114. The small hole 114 does not leave a scar.

The surgeon can use visual means inserted through the navel, hole 113.

The instrument is connected using the above detailed system of needle, rod and hook.

During the next stage, the sleeve 116 may be taken out. Preferably the sleeve is left in place, its one end secured to the virtual port at location 114, the other end remains outside the body at hole 113. This allows easier replacement of surgical tools and their placement at the precise desired location, near the hole 114 in this example, using the sleeve 116 as a guide.

The surgical tools may use various working elements.

The sleeve 116 is preferably flexible, thus it does not have a specific shape. Working elements have a thickness about 3-4 mm at their end, but are manipulated by sticks which are thinner, about 2 mm. By inserting the instruments one after the other, it is possible to insert several instruments through a relatively thin sleeve and hole in the abdomen, for example two instruments of 3.5-4 mm thickness each can be inserted through a 6 mm sleeve and hole.

Moreover, the surgical instruments can be activated, either manually or using motor means.

Figure 33:
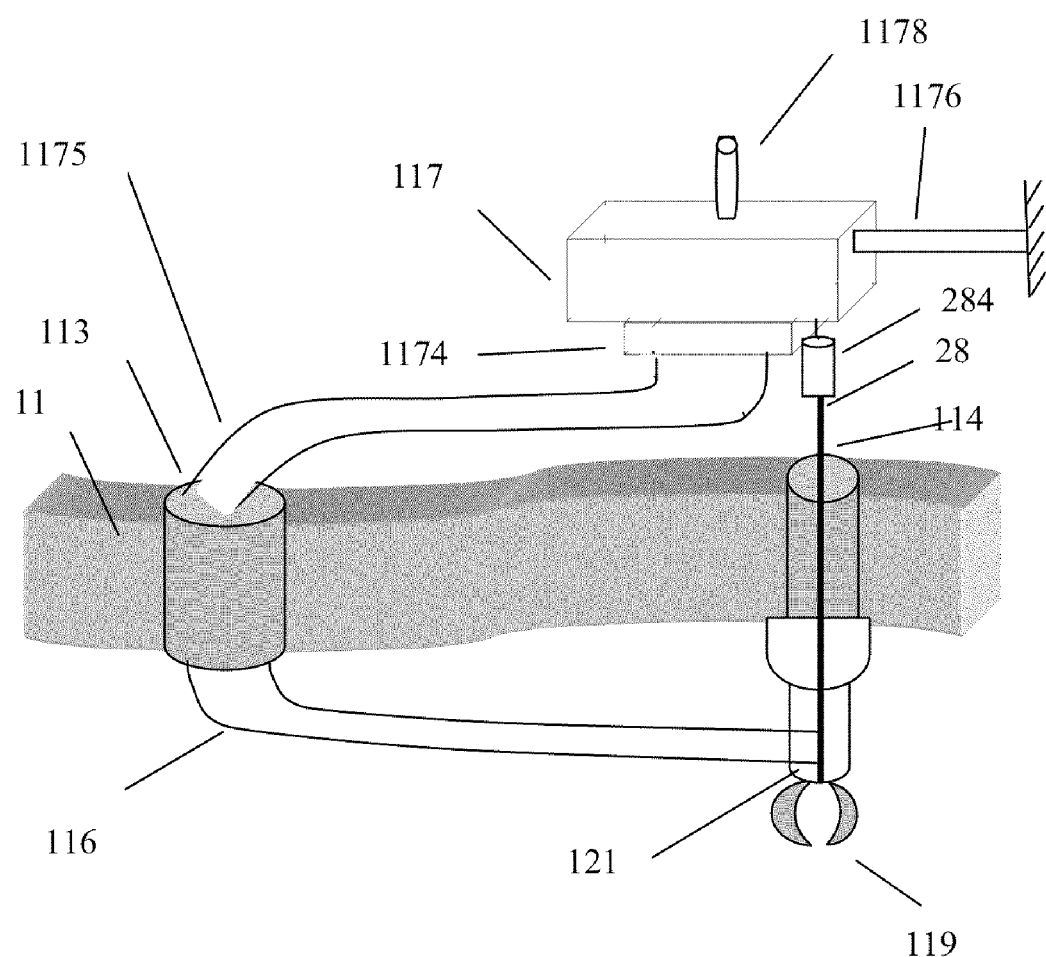
FIG. 33 details a fully motorized surgery support system

FIG. 33 details a fully motorized surgery support system. In this embodiment, the central motorized station 117 is secured in place above the virtual port 114 using means 1176.

The element or stick 28, rather than being manually handled, is connected to a motor or a plurality of motors, in the station 117. This allows the surgeon easier control over the surgical tools. The tool is held in place while the surgeon is otherwise occupied, freeing his/her hands for additional tasks. Precise movement control may be achieved using servo-control techniques as known in the art.

Activation of stick 28—by pull wires or pneumatic or hydraulic means and may have scissors at its end.

The end of stick 28 may be deflected using various means such as pull wires or hydraulic means. This adds another two dimensions 2D, achieved by that deflection.

Then, in total, the system can implement a 6D movement, six degrees of freedom for the working element.

The control site at station 117 may include a control joystick 1178, which controls it in 4D or 6D, and according to the specific implementation.

Thus, a single control site allows the surgeon complete control over the surgery, from only one place.

During a surgical intervention, surgery may be needed in several places inside the body. Accordingly, another small hole 114 may be made and a virtual port created there, and the central motorized station 117 can be moved to that location and secured in place there.

Figure 34:
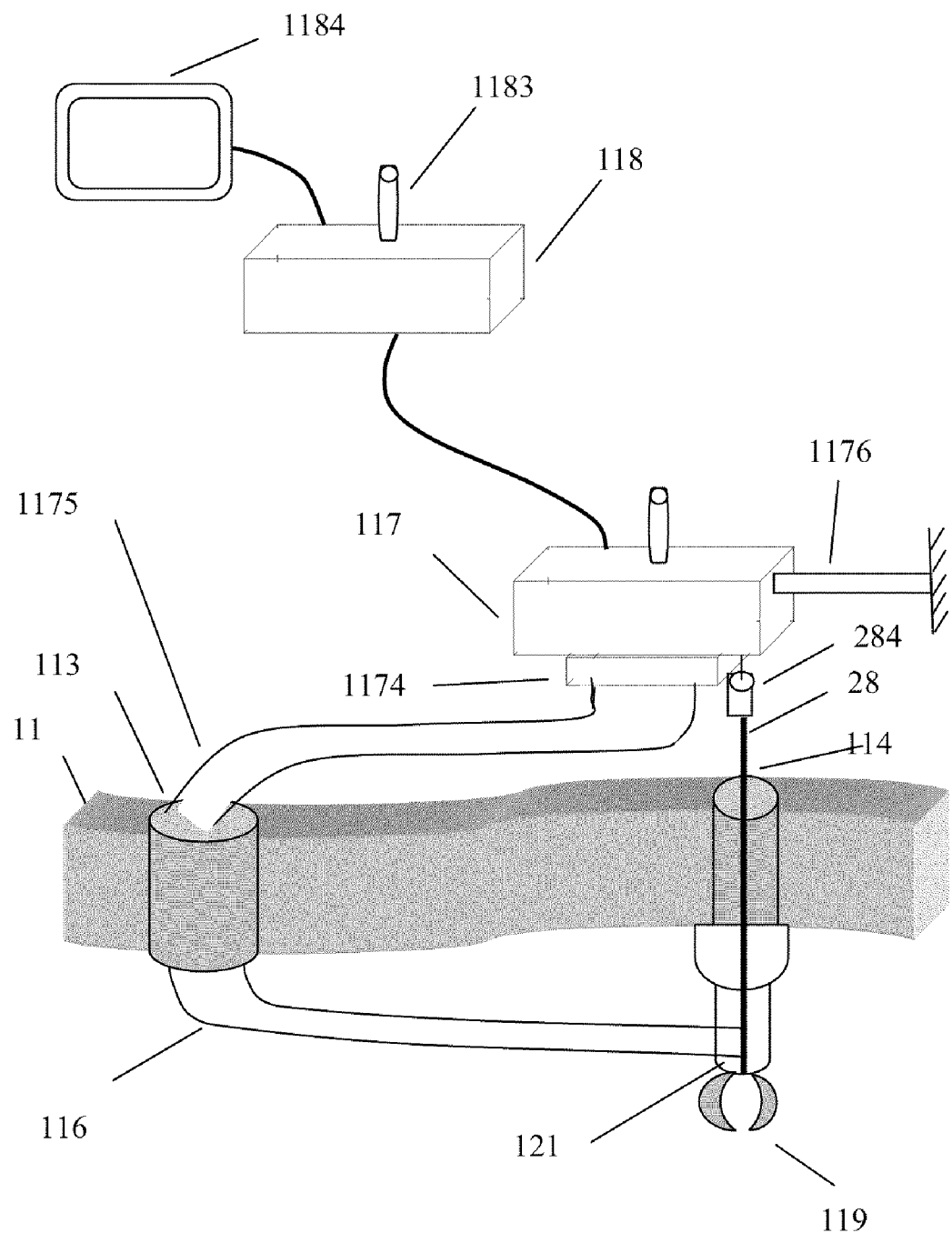
FIG. 34 details a fully motorized surgery support system using a remote control unit.

FIG. 34 details a fully motorized surgery support system using a remote control unit.

The remote control unit 118 is connected to the central motorized station 117 and has full control over its operation.

It may include a joystick 1183 and/or other control means, and display means 1184.

Unit 118 may be connected to station 117 through electrical cables to bring the desired control, information and/or electrical power as dictated by engineering considerations.

The movement of the motors in device 117 may thus be controlled from a remote place 118, preferably a desk site that needs not be close to the patient.

Thus, surgery can be performed under remote control.

A monitor or display means for the surgeon can connect to several TV cameras inside the abdomen, to achieve 3D viewing of the surgery site. Preferably use three cameras. Can use two or more than three cameras.

The surgeon at the control site 118 has complete control over the operation, can see a bi-dimensional or a tri-dimensional image of the surgery site.

The system can use special screens as known in the art, and/or special glasses for 3D viewing or virtual reality imaging.

The end of the sleeve 116 is secured in place, thus allows multiple insertions/removals/replacements of instruments therethrough.

The surgeon keeps track of the surgery location throughout the surgical procedure, which may include a plurality of instruments, using the precise locations of the virtual ports 114.

Benefit of joystick, automatic system—it is comfortable to surgeon, improves surgical performance, and may reduce the chances of human errors.

The new system takes just a small place over the patient.

Prior art systems include the "Da Vinci System" manufactured by Intuitive Motion.

A prior art system uses a large robot system, weighting about 200 kg, positioned over the patient. Such a system, should it accidentally fall down on to the patient, may crush the patient. Moreover, it may obscure the surgeon's view of the patient, hindering the desirable medical surveillance of the patient.

The new system is small, thus it will not obscure the surgeon's view of the patient. The system is lightweight, so it will not present a danger to the patient.

Prior art systems are robot-like, having two arms with fixed instruments attached thereto. It may be difficult to replace the working instruments.

The new system, however, allows easy replacement of working elements.

Prior art systems use a plurality of large abdominal holes, about 8-10 mm diameter each. The new system uses just one hole of 8-10 mm diameter, with the rest being narrow holes, about 1-2 mm diameter.

The new system uses a plurality of small motors to achieve movement in several dimensions, for example three, four or six dimensions.

This is a low cost, lightweight structure.

Prior art robot arms with transmission means, gears, pull wires—a complex, very expensive structure and to supply electrical power to the camera, working tubes for washing the surgery area for example, suction tubes.

In a preferred embodiment, washing tubes of about 1 mm diameter and/or Teflon suction tubes of about 0.9 mm may be inserted through a hole of about 5 mm diameter in the abdomen.

Method of Surgery Using a Plurality of Virtual Ports

The surgeon may use one hole 113 in the abdomen for inserting surgical instruments, and a plurality of anchoring sites 114 having a minimal diameter, for holding and manipulating these instruments.

The central motorized station 117 is secured in place above the virtual port 114 which is instantly used for surgery, using means 1176.

The station 117 may thus be secured to a fixed location 1176 such as the patient's bed or other fixture. Alternately, device 117 is placed on the patient's body directly.

The surgical elements are connected to the station 117 and are subsequently controlled from that station.

The surgeon may operate using the controls at station 117, or may connect that station to a remote control center which then controls the surgical tools.

Figure 35:
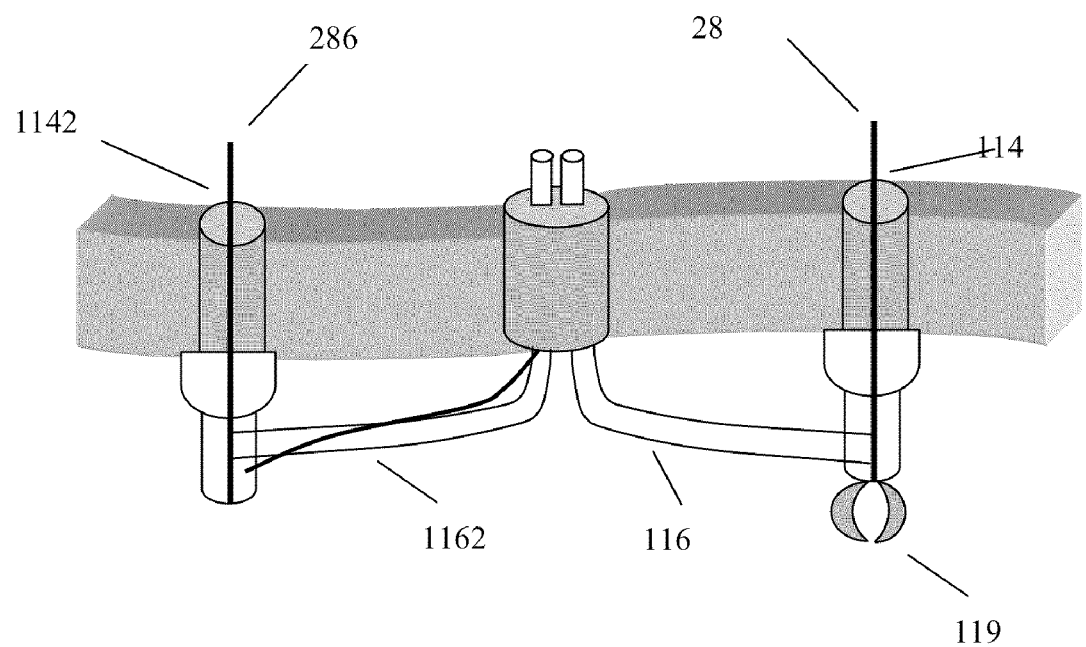
FIG. 35 details a surgery support system for concurrent operation at two sites within the patient's body.

FIG. 35 details a surgery support system for concurrent operation at two sites within the patient's body.

Concurrent surgery at two or more places is possible using the present invention.

In this embodiment, two sleeves 116, 1162 are inserted through the hole 113 in the abdominal wall. The former sleeve is connected to a surgical tool at the virtual port at location 114, whereas the latter sleeve—to the tool at location 1142.

The surgeon can use the rods 28 and 286, correspondingly, at these two locations, for the actual surgery.

Preferably, a ferrite material is used in the device inside the patient's body, to create a virtual port using magnetic fields.

An internal surgery method is disclosed, using the grasping means disclosed above.

Method for Securing Internal Organs

The method includes:
1. Attaching a first part to a first internal body surface
2. Attaching a second part to a second internal body surface
3. Applying a force between the first part and the second part, during internal surgery.
4. Releasing the force at the end of the surgery 5. Removing the first and second parts from the patient's body.

End of method.

The invention discloses a method for attaching internal organs to each other or of an organ to the underside of a body cavity.

For example, internal organs may be attached to the underside of the abdominal wall.

The method includes attaching to an organ using various means, such as a sheet, a pin, or a net. Various grasping means may be used, for example suction means, an adhesive, clips, a needle with loop/hook means, barbs or magnetic means. The grasping means may include means for re-locating the virtual port as required by the surgeon. Re-locating may be performed either invasively or non-invasively.

After attaching such means to two locations, it is possible to apply a controlled force between the secured ends of the device, to achieve retraction as required in surgery.

The method may be used to hold an organ at a desired location, or to attach it to another organ or to a body internal wall. The grasping means may include a strip coated with an adhesive material.

The adhesive-coated surface adheres easily to the surface of a body organ or the wall of a body cavity. In a preferred embodiment, the strip is only coated at specific locations, to prevent its undesired adherence to other organs.

The strip may be of a bio-degradable material, which disintegrates in about one to two months, for example. This solves the problem of a second surgery to remove the strips—they disappear by themselves.

The strips or thread of this device may be of non-absorbable material in case of blood vessels or of absorbable biodegradable material such as polylactic polygalactin acid (PLGA) in other cases and in case of retraction, or materials such as Vycril™. The adhesive may be one of the cyanoacrylates, fibrin glues or other biodegradable adhesive polymers.

The strip may be smooth or may be provided with multiple sharp barbs made of the same material in order to improve grasping and holding of tissues.

An apparatus for applying the above strip may include means for storing the strip, and means for cutting the strip after attaching it to a body organ surface as desired. In one embodiment, the strip is already coated with an adhesive and ready to use. In another embodiment, the strip is separate from the glue. The applying instrument may include means for applying the adhesive, such as a glue to be delivered at the desired location—on the organ's surface or at the strip's end—as desired. The glue may be delivered through a Teflon tube, for example, so the glue will not attach to it.

Various suction means may be used. An underpressure may be created with a vacuum pump or a Venturi device.

Magnetic means may include a ferrite powder for the part inside the body.

Method for Tissue Approximation in Internal Organs

The device with strip and adhesive can be also used for tissue approximation such as closing opening in hollow organs such as bowels, urinary bladder, blood vessels, etc. The strip may include both an adhesive and sharp barbs, for more reliable attachment to the body tissue.

The method includes:
1. Attaching a first part to a first part of an internal organ or to part of the rim of an opening thereon
2. Attaching a second part to a second part of an internal organ or to another part of the rim of an opening thereon
3. Applying a force between the first part and the second part, so as to close an opening in the organ, during internal surgery.
4. Releasing the force at the end of the surgery (optional). In another embodiment, a bio-degradable material is used, which releases the force after a prolonged time period, measured in weeks or months.
5. Removing the first and second parts from the patient's body (optional).

In another embodiment, a bio-degradable material is used. End of method.

The invention is not limited to a specific embodiment such as that using a strip. Rather, various means may be used for exerting a force between organs and/or cavity walls, including but not limited to a string, rope, netting, rod, etc.

It will be recognized that the foregoing is but one example of an apparatus and method within the scope of the present invention and that various modifications will occur to those skilled in the art upon reading the disclosure set forth hereinbefore.

What is claimed is:

1. A surgery-assisting retraction device (SARD) useful in minimally invasive surgeries for retraction of an organ within the abdominal cavity of the human body, said SARD comprising:
   a. at least one umbrella-shaped device comprising at least one hook, said hook adapted to be reversibly attached to an anchoring point on the internal abdominal wall; and,
   b. at least one wire adapted to pass through an opening within said abdominal wall at the location of said anchoring point; said at least one wire is adapted to attach said umbrella-shaped device to said anchoring point; and,
   c. at least one second anchoring means being interconnected to said at least one umbrella-shaped device via coupling means; said second anchoring means adapted to be reversibly attached to said organ within said abdominal cavity, such that when said SARD is activated, the same retracts said organ with respect to said anchoring point.

2. The SARD according to claim 1, wherein said SARD is moveable in any predetermined direction from one anchoring point to another anchoring point on said abdominal wall without creating any openings in said location of said anchoring points.

3. The SARD according to claim 1, wherein said at least one second anchoring means comprises a plurality of attachment means selected from the group consisting of: vacuum cups, magnetic means, mechanical means, adhesive means or any combination thereof; further wherein said plurality of said attachment means are adapted to homogeneously distribute mechanical load between said plurality of said attachment means.

4. The SARD according to claim 1, additionally comprising controlling means releasably attached to said SARD, adapted to (i) introduce said SARD into said abdominal cavity; (ii) to extract said SARD from said abdominal cavity; and, (iii) to relocate said SARD within said abdominal cavity; said controlling means being at least partially operated by from outside said body.

5. The SARD according to claim 1, wherein SARD is activated by an introducer.

6. The SARD according to claim 1, wherein SARD is introduced and extracted into and out of said abdominal cavity by an introducer.

7. The SARD according to claim 1, wherein SARD is manipulated and relocated within said abdominal cavity by an introducer.

8. The SARD according to claim 1, wherein said coupling means is selected from the group consisting of: a string, a tissue retractor means, a rod, or any combination thereof.

* * * * *